(12) United States Patent
Obungu et al.

(10) Patent No.: US 10,584,174 B2
(45) Date of Patent: Mar. 10, 2020

(54) ANTI-DKK-1-ANTI-RANKL BISPECIFIC ANTIBODY COMPOUNDS

(71) Applicant: Eli Lilly and Company, Indianapolis, IN (US)

(72) Inventors: Victor H Obungu, Fishers, IN (US); Andrew Korytko, Oceanside, CA (US)

(73) Assignee: Eli Lilly and Company, Indianapolis, IN (US)

( * ) Notice: Subject to any disclaimer, the term of this patent is extended or adjusted under 35 U.S.C. 154(b) by 301 days.

(21) Appl. No.: 15/570,756

(22) PCT Filed: May 12, 2016

(86) PCT No.: PCT/US2016/032108
§ 371 (c)(1),
(2) Date: Oct. 31, 2017

(87) PCT Pub. No.: WO2016/186957
PCT Pub. Date: Nov. 24, 2016

(65) Prior Publication Data
US 2018/0118840 A1 May 3, 2018

Related U.S. Application Data

(60) Provisional application No. 62/163,044, filed on May 18, 2015.

(51) Int. Cl.
| | | |
|---|---|---|
| *A61K 39/395* | (2006.01) |
| *C07K 16/18* | (2006.01) |
| *C07K 14/51* | (2006.01) |
| *C07K 16/28* | (2006.01) |
| *C07K 16/46* | (2006.01) |
| *A61P 19/00* | (2006.01) |
| *A61P 19/08* | (2006.01) |
| *A61P 19/10* | (2006.01) |
| *A61K 39/00* | (2006.01) |

(52) U.S. Cl.
CPC .......... *C07K 16/2875* (2013.01); *A61P 19/00* (2018.01); *A61P 19/08* (2018.01); *A61P 19/10* (2018.01); *C07K 16/18* (2013.01); *C07K 16/468* (2013.01); *A61K 2039/505* (2013.01); *C07K 2317/31* (2013.01); *C07K 2317/56* (2013.01); *C07K 2317/565* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,740,522 B2 | 5/2004 | Anderson | |
| 8,148,498 B2 | 4/2012 | Chedid et al. | |
| 8,338,576 B2 | 12/2012 | Paralkar et al. | |
| 10,150,800 B2 * | 12/2018 | Roschke | C07K 16/24 |
| 2010/0117980 A1 * | 5/2010 | Lee | G02F 1/13338 345/173 |
| 2013/0052199 A1 * | 2/2013 | Shaughnessy, Jr. | C07K 16/18 424/139.1 |

FOREIGN PATENT DOCUMENTS

| | | |
|---|---|---|
| WO | 2006/015373 A2 | 2/2006 |
| WO | 2010/117980 A1 | 10/2010 |
| WO | 2012/118903 A2 | 9/2012 |
| WO | 2014/081955 A1 | 5/2014 |

OTHER PUBLICATIONS

Jelinek et al., Monoclonal antibodies—A new era in the treatment of multiple myeloma, Blood Rev. 30:101-110, 2016.*
Sri Harsha Tella, et al. "Biological agents in management of osteoporosis", European Journal of Clinical Pharmacy., vol. 71, No. 11, Nov. 11, 2014, 1291-1301.
Kabat, et al., Ann. NY Acad. Sci. 190:382-93 (1971).
North et al., A New Clustering of Antibody CDR Loop Conformations, Journal of Molecular Biology, 406:228-256 (2011).
Li, Xiaodong, et al, "Dickkopf-1 Regulates Bone Formation in Young Growing Rodents and Upon Traumatic Injury"; JBMR. vol. 2g., No. 11, Nov. 2011, pp. 2610-2612.

* cited by examiner

*Primary Examiner* — Claire Kaufman
(74) *Attorney, Agent, or Firm* — Robert L Sharp

(57) ABSTRACT

Bispecific antibody compounds, and methods of using same, are provided which bind and neutralize Dkk-1 and RANKL and which are useful as adjuncts to spinal fusion surgery or as agents for bone healing or treating conditions associated with bone loss or degeneration.

12 Claims, No Drawings
Specification includes a Sequence Listing.

ANTI-DKK-1-ANTI-RANKL BISPECIFIC ANTIBODY COMPOUNDS

The present invention is in the field of medicine. More particularly, the present invention relates to bispecific antibody compounds directed against Dickkopf-related protein 1 (Dkk-1) and receptor activator of nuclear factor kappa-B ligand (RANKL). The bispecific antibody compounds of the present invention are expected to be useful in bone healing, for example as an adjunct to spinal fusion surgery and/or in the treatment of osteoporosis, osteopenia, degenerative lumbar spondylolisthesis, degenerative disk disease, osteogenesis imperfecta, or low bone mass disorders.

Bone disorders affect millions of individuals, often causing painful and debilitating symptoms. Some disorders such as osteoporosis, osteopenia, and/or osteogenesis imperfecta may require therapeutic intervention such as an agent which reduces bone resorption and/or increases bone formation. Other disorders, such as degenerative lumbar spondylolisthesis and degenerative disk disease may require therapeutic intervention such as spinal fusion surgery. Spinal fusion is a surgical procedure in which a graft substance e.g., a bone graft) is inserted between adjacent vertebrae such that the vertebrae fuse thereby limiting or eliminating the range of motion in the joint space between the fused vertebrae. In addition to the above bone disorders, spinal fusions are performed to address pain and morbidity associated with degenerative conditions such as degenerative disc disease (DDD), spondylosis, and spondylolisthesis; congenital deformities, including kyphosis and scoliosis; as well as some vertebral fractures.

Specific types of spinal fusion procedures include posterolateral lumbar fusion (PLF) and interbody fusion (for example, anterior lumbar interbody fusion (ALIF), posterior lumbar interbody fusion (PLIF), and transforaminal lumbar interbody fusion (TLIF) which differ according to location and angle of approach to the spine). PLF involves placing a graft substance between the transverse processes of adjacent lumbar vertebrae in the posterior of the spine and then securing the vertebrae to metal rods positioned on each side of the vertebrae. Interbody fusion involves removing an intervertebral disc and placing the graft substance into the intervertebral space between adjacent vertebrae, whereby fusion occurs between the graft and the endplates of the adjacent vertebrae. As with PLF, interbody fusion procedures may be stabilized by securing the vertebrae with metal rods, plates, screws, or wire.

During a spinal fusion procedure, a bone graft substitute (BGS) may also be applied to the graft and at the junction between the graft and adjacent vertebrae in order to stimulate new bone growth and fusion between the graft and vertebrae. BGSs often take the form of a moldable gel, putty, paste, or sponge and comprise substances such as bone forming proteins (e.g., bone morpohogenic proteins) and other growth factors (e.g., TGF-beta, PDGF, FGF). Although BGSs provide a means for supplying needed protein necessary for stimulating new bone formation and fusion, harvesting of BGSs presents challenges and BGSs can only be applied during the spinal fusion procedure.

Although spinal fusion procedures have been performed since the early twentieth century, such procedures continue to pose significant risk. Common risks include risk of vertebrae fusion failure (pseudoarthrosis) and the need for revision surgery, post-operative pain and morbidity, and risk of infection which can all lead to potentially long recovery times and increased patient costs. Thus, there remains a need for alternative therapies which could lead to better outcomes for patients. In particular, there remains a need for a systemically-administered pharmaceutical agent which could be used as an adjunct therapy to spinal fusion procedures. Preferably, such systemically-administered pharmaceutical agent will be capable of being administered prior to, during and/or after a spinal fusion procedure. Additionally, such alternative therapy will preferably be capable of demonstrating efficacy in reducing the risks and/or complications associated with spinal fusion procedures and/or in the treatment of osteoporosis, osteopenia, degenerative lumbar spondylolisthesis, degenerative disk disease, or osteogenesis imperfecta. The bispecific antibody compounds of the present invention, directed against Dkk-1 and RANKL, provide an alternative therapy which is expected to meet at least one of the above needs.

Dkk-1 is a member of the Dickkopf family of proteins which binds low-density lipoprotein receptor-related proteins 5/6 (LRP5/6) and disrupts the association of LRP5/6 with Wnt-family protein complexes. Studies have shown that by disrupting the binding of LRP5/6 to Wnt-family proteins, Dkk-1 inhibits the Wnt signaling pathway thereby impairing osteoblastogenesis and bone metabolism. The role played by Dkk-1 in antagonizing the Wnt signaling pathway makes it a viable target for bone formation and repair therapies.

RANKL is a member of the TNF-superfamily of proteins and plays a critical role in bone remodeling. RANKL is expressed by osteoblasts and binds its cognate receptor RANK on the surface of osteoclasts and osteoclast precursor cells. Binding of RANKL to RANK induces the formation, activation, and survival of mature osteoclasts and the stimulation of intracellular signaling cascades leading to increased bone resorption. Because of its role in bone resorption, inhibition of RANKL is recognized as a mechanism for improving bone mineral density in patients.

Neutralizing antibodies to Dkk-1 and RANKL are known in the art. For example, U.S. Pat. No. 8,148,498 discloses Dkk-1 antibodies for use in bone healing and treating cancers. Likewise, U.S. Pat. No. 6,740,522 discloses antibodies directed against RANKL, such as Denosumab which is approved for the treatment of osteoporosis in postmenopausal women and men at high risk for fracture. Additionally, U.S. Pat. No. 8,338,576 discusses possible combination therapies including a Dkk-1 antibody and one of various bone anabolic or anti-resorptive agents, including RANKL inhibitors, for the treatment of bone mass disorders. However, there is no approved combined therapy for inhibiting the activity of both Dkk-1 and RANKL. Thus, there remains a need for an alternative therapy that combines the bone formation properties of a Dkk-1 inhibitor with the anti-bone resorptive properties of a RANKL inhibitor and improves bone healing outcomes in patients such as spinal fusion patients.

One approach to such an alternative therapy may include the co-administration of two different bioproducts (e.g., antibodies). Co-administration requires either injections of two separate products or a single injection of a co-formulation of two different antibodies. While two injections permit flexibility of dose amounts and timing, it is inconvenient to patients both for compliance and pain. Further, while a co-formulation might provide some flexibility of dose amounts, it is often quite challenging or impossible to find formulation conditions having acceptable viscosity in solution (at relatively high concentration) and that permit chemical and physical stability of both antibodies due to different molecular characteristics of the two antibodies. Additionally, co-administration and co-formulation involve the additive costs of two different drug therapies which can increase patient and/or pay or costs. As such, there remains a need for alternative therapies for the treatment of bone disorders and preferably such alternative therapies will comprise a bispecific antibody. However, despite the disclosure of anti-Dkk-1 and anti-RANKL antibodies described above, a single neutralizing bispecific antibody that binds both Dkk-1 and RANKL has not been disclosed in the prior art.

The present invention addresses the need for an alternative therapy for bone fusion procedures. More particularly, the present invention provides bispecific antibody compounds capable of inhibiting the activity of both Dkk-1 and RANKL. The bispecific antibody compounds of the present invention provide a pharmaceutical agent suitable for systemic administration and which is capable of being administered prior to, during, and/or after a spinal fusion procedure. Furthermore, the bispecific antibody compounds of the present invention are useful as agents for bone healing, for example as an adjunct to spinal fusion procedures or in treating conditions associated with bone loss or degeneration.

The present invention provides bispecific antibody compounds having four polypeptide chains, two first polypeptide chains and two second polypeptide chains, wherein each first polypeptide chain comprises a single chain variable fragment (scFv) independently linked at the C-terminus of a mAb IgG heavy chain (HC) via a polypeptide linker (L1) and each of the second polypeptide chains comprises a mAb light chain (LC). According to bispecific antibody compounds of the present invention, each HC comprises a heavy chain variable region (HCVR1) with heavy chain complementarity determining regions (HCDRs) 1-3 and each LC comprises a light chain variable region (LCVR1) with light chain complementarity determining regions (LCDRs) 1-3. Additionally, according to bispecific antibody compounds of the present invention, each scFv comprises a light chain variable region (LCVR2) with LCDRs 4-6 and a heavy chain variable region (HCVR2) with HCDRs 4-6. Also, according to bispecific antibody compounds of the present invention, HCVR2 is linked at its N-terminus to L1 and linked at its C-terminus to a polypeptide linker (L2) which is linked to the N-terminus of LCVR2. According to particular embodiments of bispecific antibody compounds of the present invention, the amino acid sequence of HCDR1 is given by SEQ ID NO: 9, the amino acid sequence of HCDR2 is given by SEQ ID NO: 10, the amino acid sequence of HCDR3 is given by SEQ ID NO: 11, the amino acid sequence of LCDR1 is given by SEQ ID NO: 15, the amino acid sequence of LCDR2 is given by SEQ ID NO: 16, the amino acid sequence of LCDR3 is given by SEQ ID NO: 17, the amino acid sequence of HCDR4 is given by SEQ ID NO: 12, the amino acid sequence of HCDR5 is given by SEQ ID NO: 13, the amino acid sequence of HCDR6 is given by SEQ ID NO: 14, the amino acid sequence of LCDR4 is given by SEQ ID NO: 18, the amino acid sequence of LCDR5 is given by SEQ ID NO: 19, and the amino acid sequence of LCDR6 is given by SEQ ID NO: 20. In some more particular embodiments, the HC comprises a mAb IgG4 isotype and each LC comprises a mAb kappa light chain.

In some particular embodiments, the present invention provides bispecific antibody compounds having four polypeptide chains, two first polypeptide chains and two second polypeptide chains, wherein each first polypeptide chain comprises a scFv independently linked at the C-terminus of a HC via L1 and each of the second polypeptide chains comprises a LC. According to such embodiments, each HC comprises a HCVR1 having an amino acid sequence given by SEQ ID NO: 5 and each LC comprises a LCVR1 having an amino acid sequence given by SEQ ID NO: 7. Additionally, each scFv comprises a HCVR2 having an amino acid sequence given by SEQ ID NO: 6 and a LCVR2 having an amino acid sequence given by SEQ ID NO: 8. According to bispecific antibodies of the present invention, HCVR2 is linked at its N-terminus to L1 and linked at its C-terminus to L2 which is linked to the N-terminus of LCVR2. In some even more particular embodiments, the amino acid sequence of L1 is given by SEQ ID NO: 21 and the amino acid sequence of L2 is given by SEQ ID NO: 22.

According to further particular embodiments, the present invention provides bispecific antibody compounds having four polypeptide chains, two first polypeptide chains and two second polypeptide chains, wherein the amino acid sequence of each first polypeptide chain is given by SEQ ID NO: 1 and wherein the amino acid sequence of each second polypeptide chain is given by SEQ ID NO: 2.

The present invention also relates to nucleic acid molecules and expression vectors encoding bispecific antibody compounds of the present invention. In an embodiment, the present invention provides a DNA molecule comprising a polynucleotide sequence encoding the first polypeptide chain, wherein the amino acid sequence of the first polypeptide chain is SEQ ID NO: 1. In an embodiment, the present invention also provides a DNA molecule comprising a polynucleotide sequence encoding the second polypeptide chain, wherein the amino acid sequence of the second polypeptide chain is SEQ ID NO: 2. In a further embodiment, the present invention provides a DNA molecule comprising a polynucleotide sequence encoding the first polypeptide chain having the amino acid sequence of SEQ ID NO:1, and comprising a polynucleotide sequence encoding the second polypeptide chain having the amino acid sequence of SEQ ID NO:2. In a particular embodiment the polynucleotide sequence encoding the first polypeptide chain having the amino acid sequence of SEQ ID NO:1 is given by SEQ ID NO:3 and the polynucleotide sequence encoding the second polypeptide chain having the amino acid sequence of SEQ ID NO:2 is given by SEQ ID NO:4.

The present invention also provides a mammalian cell transformed with DNA molecule(s) which cell is capable of expressing a bispecific antibody compound comprising the first polypeptide chain and the second polypeptide chain of the present invention. Also, the present invention provides a process for producing a bispecific antibody compound comprising the first polypeptide chain and the second polypeptide chain, comprising cultivating the mammalian cell under conditions such that a bispecific antibody compound of the present invention is expressed. The present invention also provides a bispecific antibody compound produced by said process.

The present invention also provides a pharmaceutical composition comprising a bispecific antibody compound of the present invention and one or more pharmaceutically acceptable carriers, diluents, or excipients. Pharmaceutical compositions of the present invention can be used in the treatment of a spinal fusion patient, whereby such treatment comprises administering to a spinal fusion patient a pharmaceutical composition of the present invention prior to, during, and/or after spinal fusion surgery. In some embodiments, pharmaceutical compositions of the present invention can be used in the treatment of a bone disorder. In some embodiments, pharmaceutical compositions of the present invention can be used in the treatment of at least one of osteoporosis, osteopenia, degenerative lumbar spondylolisthesis, degenerative disk disease, and/or osteogenesis imperfecta whereby such treatment comprises administering to a patient in need thereof a pharmaceutical composition of the present invention.

The present invention also provides a method of treating a spinal fusion patient comprising administering to a spinal fusion patient a therapeutically effective amount of a bispecific antibody compound of the present invention or pharmaceutical composition thereof, wherein said bispecific antibody compound or pharmaceutical composition thereof is administered to said spinal fusion patient prior to, during, and/or after spinal fusion surgery. Additionally, the present invention provides a method of treating a bone disorder comprising, administering to a patient in need thereof a therapeutically effective amount of a bispecific antibody compound of the present invention. Further embodiments of the present invention provide a method of treating at least one of osteoporosis, osteopenia, degenerative lumbar spondylolisthesis, degenerative disk disease, and/or osteogenesis imperfecta comprising administering to a patient in need thereof a therapeutically effective amount of a bispecific antibody compound of the present invention or pharmaceutical composition thereof.

The present invention also provides a bispecific antibody compound of the present invention or pharmaceutical composition thereof for use in therapy. More particularly, the present invention also provides a bispecific antibody compound of the present invention or pharmaceutical composition thereof for use in the treatment of a spinal fusion patient. Additionally, the present invention provides a bispecific antibody compound of the present invention or pharmaceutical composition thereof for use in the treatment of a bone disorder. Further, the present invention provides a bispecific antibody compound of the present invention or pharmaceutical composition thereof for use in the treatment of at least one of osteoporosis, osteopenia, degenerative lumbar spondylolisthesis, degenerative disk disease, and/or osteogenesis imperfecta.

In an embodiment, the present invention also provides the use of a bispecific antibody compound of the present invention or a pharmaceutical composition thereof in the manufacture of a medicament for the treatment of a spinal fusion patient. Additionally, the present invention also provides a bispecific antibody compound of the present invention or pharmaceutical composition thereof in the manufacture of a medicament for the treatment of a bone disorder. Further, the present invention also provides a bispecific antibody compound of the present invention or pharmaceutical composition thereof in the manufacture of a medicament for the treatment of at least one of osteoporosis, osteopenia, degenerative lumbar spondylolisthesis, degenerative disk disease, and/or osteogenesis imperfecta.

As referred to herein, the term "bispecific antibody compound" refers to an engineered polypeptide comprising four antigen binding sites. Two of the four antigen binding sites bind Dkk-1 and the other two antigen binding sites bind RANKL. A bispecific antibody compound of the present invention is capable of interacting with, and inhibiting the activity of both human Dkk-1 and RANKL alone or simultaneously. In combining Dkk-1 and RANKL inhibitory properties into a single compound, it is believed that the bispecific antibody compounds of the present invention will demonstrate bone formation and/or anti-bone resorptive effects in patients. Thus, the bispecific antibody compounds of the present invention, or pharmaceutical compositions thereof, may be useful, for example, as adjuncts to spinal fusion surgery and/or in the treatment of one or more bone disorders.

Also, a bispecific antibody compound, as referred to herein, comprises four polypeptide chains, two first polypeptide chains and two second polypeptide chains. Each of the first polypeptide chains is engineered to comprise a single chain variable fragment (scFv) linked at the C-terminus of a mAb heavy chain (HC) by a polypeptide linker (L1). Each of the second polypeptide chains is engineered to comprise a mAb light chain (LC) and form inter-chain disulfide bonds with one of the first polypeptide chains, specifically within the HC of a first polypeptide chain. Each first polypeptide chain is engineered to form inter-chain disulfide bonds with the other first polypeptide chain, specifically between the HC of each of the first polypeptide chains. Each first polypeptide chain is further engineered to form intra-chain disulfide bonds, specifically within the scFv of each respective first polypeptide chain.

The polypeptide chains of the bispecific antibody compounds of the present invention are depicted by their sequence of amino acids from N-terminus to C-terminus, when read from left to right, with each amino acid represented by either its single letter or three-letter amino acid abbreviation. Unless otherwise stated herein, all amino acids used in the preparation of the polypeptides of the present invention are L-amino acids. The "N-terminus" (or amino terminus) of an amino acid, or a polypeptide chain, refers to the free amine group on the amino acid, or the free amine group on the first amino acid residue of the polypeptide chain. Likewise, the "C-terminus" (or carboxy terminus) of an amino acid, or a polypeptide chain, refers to the free carboxy group on the amino acid, or the free carboxy group on the final amino acid residue of the polypeptide chain.

As referred to herein, a "single chain variable fragment" (scFv) of a first polypeptide chain, refers to a polypeptide chain comprising a heavy chain variable region (HCVR2) and a light chain variable region (LCVR2) linked via a polypeptide linker (L2). Additionally, as referred to herein (and as represented in the following schematic), the HCVR2 of each scFv is: a.) linked, at its N-terminus, to the C-terminus of one HC (of a first polypeptide chain) by a polypeptide linker (L1); and b.) linked, at its C-terminus, to the N-terminus of the LCVR2 of the same scFv via a second polypeptide linker (L2). Linkers L1 and L2 are typically of about 10 to 25 amino acids in length and rich in one or more of glycine, serine or threonine amino acids.

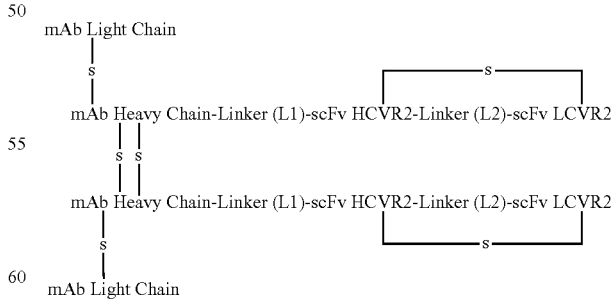

According to bispecific antibody compounds of the present invention, the HC of each first polypeptide chain is classified as gamma, which defines the isotype (e.g., as an IgG). The isotype may be further divided into subclasses (e.g., $IgG_1$, $IgG_2$, $IgG_3$, and $IgG_4$). In particular embodiments, bispecific antibody compounds of the present invention comprise mAb heavy chains of the IgG4 type. Each HC is comprised of an N-terminal heavy chain variable region followed by a constant region (CH), comprised of three domains ($C_H1$, $C_H2$, and $C_H3$) and a hinge region.

Additionally, according to bispecific antibody compounds of the present invention each mAb light chain (LC) is classified as kappa or lambda and characterized by a particular constant region as known in the art. In particular embodiments the bispecific antibody compounds of the present invention comprise kappa LCs. Each LC is comprised of an N-terminal light chain variable region (LCVR1) followed by a light chain constant region.

The HCVR1 and LCVR1, of each HC and LC respectively, and HCVR2 and LCVR2, of each scFv, can be further subdivided into regions of hypervariability, termed complementarity determining regions (CDRs), interspersed with regions that are more conserved, termed framework regions (FR). Preferably, the framework regions of the bispecific antibody compounds of the present invention are of human origin or substantially of human origin. Each HCVR1, HCVR2, LCVR1, and LCVR2 of bispecific antibody compounds according to the present invention are composed of three CDRs and four FRs, arranged from amino-terminus to carboxy-terminus in the following order: FR1, CDR1, FR2, CDR2, FR3, CDR3, FR4. Herein the 3 CDRs of each HCVR1 are referred to as "HCDR1, HCDR2, and HCDR3;" the 3 CDRs of each HCVR2 are referred to as "HCDR4, HCDR5, and HCDR6;" the 3 CDRs of each LCVR1 are referred to as "LCDR1, LCDR2, and LCDR3;" and the 3 CDRs of each LCVR2 are referred to as "LCDR4, LCDR5, and LCDR6." The CDRs contain most of the residues which form specific interactions with the antigen. The functional ability of a bispecific antibody compound of the present invention to bind a particular antigen is largely influenced by the CDRs.

As used interchangeably herein, "antigen-binding site" and "antigen-binding region" refers to those portions of bispecific antibody compounds of the present invention which contain the amino acid residues that interact with an antigen and confer to the bispecific antibody compound specificity and affinity for a respective antigen. According to bispecific antibody compounds of the present invention, antigen-binding sites are formed by a HCVR1/LCVR1 pair (of a LC and HC bound by inter-chain disulfide bonds) and by a scFv HCVR2/LCVR2 pair. Additionally, according to bispecific antibody compounds of the present invention, antigen-binding sites formed by each HCVR1/LCVR1 pair are the same (e.g., comprises affinity for a same antigen), and antigen-binding sites formed by each scFv HCVR2/LCVR2 pair are the same (e.g., comprises affinity for a same antigen). However, according to bispecific antibody compounds of the instant invention, antigen-binding sites formed by each HCVR1/LCVR1 pair are different (e.g., comprises affinity for a different antigen) from antigen-binding sites formed by each scFv HCVR2/LCVR2 pair. According to bispecific antibody compounds of the present invention, the antigen-binding site formed by a HCVR1/LCVR1 pair confers affinity for Dkk-1, whereas the antigen-binding site formed by a HCVR2/LCVR2 pair confers affinity for RANKL.

The terms "Kabat numbering" or "Kabat labeling" are used interchangeably herein. These terms, which are recognized in the art, refer to a system of numbering amino acid residues which are more variable (i.e., hypervariable) than other amino acid residues in the heavy chain and light chain variable regions of an antibody (Kabat, et al., *Ann. NY Acad. Sci.* 190:382-93 (1971); Kabat et al., *Sequences of Proteins of Immunological Interest*, Fifth Edition, U.S. Department of Health and Human Services, NIH Publication No. 91-3242 (1991)).

The terms "North numbering" or "North labeling" are used interchangeably herein. These terms, which are recognized in the art, refer to a system of numbering amino acid residues which are more variable (i.e., hypervariable) than other amino acid residues in the heavy and light chains variable regions of an antibody and is based, at least in part, on affinity propagation clustering with a large number of crystal structures, as described in (North et al., *A New Clustering of Antibody CDR Loop Conformations*, Journal of Molecular Biology, 406:228-256 (2011).

Bispecific Antibody Engineering

Significant issues were encountered when attempting to construct a bispecific antibody compound of the present invention. Problems encountered included engineering a single agent which possesses compatible and/or optimal bioactivity for both an increase in bone formation and a decrease in bone resorption. For example, a bispecific antibody compound comprising a Dkk-1 antibody (described in U.S. Pat. No. 8,148,498) as one of the mAb or scFv portions, and a known RANKL antibody (such as Denosumab) as the other of the mAb or scFv portions, does not provide an agent having compatible and/or acceptable bioactivity. In fact, studies have shown the pharmacodynamic effect profile of Denosumab (for decreasing bone resorption) is six months and the half-life is approximately 35-42 days, whereas the pharmacodynamic effect profile of a Dkk-1 antibody as described in U.S. Pat. No. 8,148,498 (for increasing bone formation) is one month and the half-life is only approximately 16 days. Such disparate biological activity profiles create an issue for dosing, especially for therapeutic use as an adjunct to spinal fusion therapy (where essential bone healing and fusion are known to take place in the first three months post-surgery). As such, in order to arrive at a bispecific antibody compound possessing the surprising and unexpected characteristics of the present invention, pharmacological intervention is needed.

As a result of the significant issues detailed above relating to engineering a bispecific antibody compound of the present invention, in order to arrive at a therapeutic bispecific antibody possessing a bioactivity profile acceptable for use as an adjunct to spinal fusion surgery, a novel RANKL antibody was developed and engineered. As such, a bispecific antibody compound comprising a Dkk-1 mAb portion and a RANKL scFv portion (described in further detail herein) was engineered. The engineered bispecific antibody compounds of the present invention comprise therapeutically acceptable and compatible bioactivity profiles for bone resorption (decrease) and bone formation (increase) for use as an adjunct to spinal fusion surgery. Additionally and surprisingly, the engineered modifications resulted in a bispecific antibody also possessing therapeutically acceptable stability, solubility, photostability, thermostability, and viscosity. None of the modifications resulting in the bispecific antibody compounds of the present invention are routine or common general knowledge suggested or taught in the art.

Bispecific Antibody Expression

Expression vectors capable of directing expression of genes to which they are operably linked are well known in the art. Expression vectors can encode a signal peptide that facilitates secretion of the polypeptide(s) from a host cell. The signal peptide can be an immunoglobulin signal peptide or a heterologous signal peptide. Each of the first polypeptide chains and the second polypeptide chains may be expressed independently from different promoters to which they are operably linked in one vector or, alternatively, the first and second polypeptide chains may be expressed independently from different promoters to which they are operably linked in two vectors—one expressing the first polypeptide chain and one expressing the second polypeptide chain. Exemplary suitable vectors for use in preparing bispecific antibody compounds of the present invention include vectors available from Lonza Biologics such as pEE 6.4 (for expressing the first polynucleotide sequence for example) and pEE 12.4 (for expressing the second polynucleotide sequence for example).

A particular DNA polynucleotide sequence encoding an exemplified first polypeptide chain (comprising a scFv linked at the C-terminus of a HC via a flexible glycine serine linker) of a bispecific antibody compound of the present invention having the amino acid sequence of SEQ ID NO: 1 is provided by SEQ ID NO: 3 (the DNA polynucleotide sequence provided by SEQ ID NO: 3 also encodes a signal peptide). A particular DNA polynucleotide sequence encoding an exemplified second polypeptide chain (comprising a LC) of a bispecific antibody compound of the present invention having the amino acid sequence of SEQ ID NO: 2 is provided by SEQ ID NO: 4 (the DNA polynucleotide sequence provided by SEQ ID NO: 4 also encodes a signal peptide).

A host cell includes cells stably or transiently transfected, transformed, transduced, or infected with one or more expression vectors expressing a first polypeptide chain, a second polypeptide chain or both a first and a second polypeptide chain of the present invention. Creation and isolation of host cell lines producing a bispecific antibody compound of the present invention can be accomplished using standard techniques known in the art. Mammalian cells are preferred host cells for expression of bispecific antibodies. Particular mammalian cells are CHO, NS0, DG-44 and HEK 293. Preferably, the bispecific antibody compounds are secreted into the medium in which the host cells are cultured, from Which the bispecific antibody compounds can be recovered or purified by conventional techniques. For example, the medium may be applied to and eluted from a Protein A or G affinity chromatography column and size exclusion or Capto multimodal chromatography using conventional methods. Additionally, soluble aggregate and multimers may be effectively removed by common techniques, including size exclusion, hydrophobic interaction, ion exchange, or hydroxyapatite chromatography. The product may be immediately frozen, for example at −70° C., or may be lyophilized.

It is well known in the art that mammalian expression of antibodies results in glycosylation. Typically, glycosylation occurs in the Fc region of the antibody at a highly conserved N-glycosylation site. N-glycans typically attach to asparagine. By way of example, each HC of the exemplified bispecific antibody compound presented in Table 1 (below) is glycosylated at asparagine residue 296 of SEQ ID NO: 1.

Therapeutic Uses

As used herein, "treatment" and/or "treating" are intended to refer to all processes wherein there may be a slowing, interrupting, arresting, controlling, or stopping of the progression of the disorders described herein, but does not necessarily indicate a total elimination of all disorder symptoms. Treatment includes administration of a bispecific antibody compound of the present invention, or pharmaceutical composition thereof, for treatment of a disease or condition in a patient that would benefit from a decreased level of Dkk-1 and/or RANKL or decreased bioactivity of Dkk-1 and/or RANKL, and includes: (a) inhibiting further progression of the disease, i.e., arresting its development; and (b) relieving the disease, i.e., causing regression of the disease or disorder or alleviating symptoms or complications thereof. The bispecific antibody of the present invention is expected to be useful in bone healing, for example as an adjunct to spinal fusion surgery and/or in the treatment of osteoporosis, osteopenia, degenerative lumbar spondylolisthesis, degenerative disk disease, or osteogenesis imperfecta.

The terms "patient," "subject," and "individual," used interchangeably herein, refer to a human. In some embodiments, a patient is a human that has been diagnosed as in need of, is undergoing, or has previously undergone a spinal fusion procedure. In some embodiments, a patient is a human that is characterized as being at risk of needing or in need of bone healing, for example bone building, bone remodeling, fracture repair, prevention of hone loss of degeneration, and/or as being at risk of developing or in need of treatment for a bone disorder such as osteoporosis, osteopenia, degenerative lumbar spondylolisthesis, degenerative disk disease, or osteogenesis imperfecta.

Pharmaceutical Composition

Bispecific antibody compounds of the present invention can be incorporated into a pharmaceutical composition suitable for administration to a patient. The bispecific antibody compounds of the present invention are intended for administration via parental routes including, intravenous, intramuscular, subcutaneous, or intraperitoneal. Additionally, bispecific antibody compounds of the present invention may be administered to a patient alone or with a pharmaceutically acceptable carrier and/or diluent in single or multiple doses. Such pharmaceutical compositions are designed to be appropriate for the selected mode of administration, and pharmaceutically acceptable diluents, carriers, and/or excipients such as dispersing agents, buffers, surfactants, preservatives, solubilizing agents, isotonicity agents, stabilizing agents and the like are used as appropriate. Said compositions can be designed in accordance with conventional techniques disclosed in, e.g., Remington, *The Science and Practice of Pharmacy,* 19$^{th}$ Edition, Gennaro, Ed., Mack Publishing Co., Easton, Pa. 1995 Which provides a compendium of formulation techniques as are generally known to practitioners. Suitable carriers for pharmaceutical compositions include any material which, when combined with a bispecific antibody compound of the present invention, retains the molecule's activity and is non-reactive with the patient's immune system. A pharmaceutical composition of the present invention comprises a bispecific antibody compound and one or more pharmaceutically acceptable carriers, diluents, or excipients.

An effective amount of a bispecific antibody compound of the present invention refers to an amount necessary (at dosages and for periods of time and for the means of administration) to achieve the desired therapeutic result. An effective amount of the bispecific antibody compound or pharmaceutical composition thereof may vary according to factors such as the disease state, age, sex, and weight of the individual, and the ability of the bispecific antibody compound or portion(s) thereof to elicit a desired response in the individual. An effective amount is also one in which any toxic or detrimental effect of the bispecific antibody compound is outweighed by the therapeutically beneficial effects.

EXAMPLES

Bispecific Antibody Expression and Purification

An exemplified bispecific antibody of the present invention is expressed and purified essentially as follows. A glutamine synthetase (GS) expression vector containing the DNA of SEQ ID NO: 3 (encoding an exemplified first polypeptide chain of SEQ ID NO: 1 and a post-translationally cleaved signal peptide) and SEQ ID NO: 4 (encoding an exemplified second polypeptide chain of SEQ ID NO: 2 and a post-translationally cleaved signal peptide) is used to transfect a Chinese hamster cell line (CHO, GS knockout), by electroporation. The expression vector encodes a SV Early (Simian Virus 40E) promoter and the gene for GS. Expression of GS allows for the biochemical synthesis of glutamine, an amino acid required by the CHO cells. Post-transfection, cells undergo bulk selection with 50 μM L-methionine sulfoximine (MSX). The inhibition of GS by MSX is utilized to increase the stringency of selection. Cells with integration of the expression vector cDNA into transcriptionally active regions of the host cell genome can be selected against CHO wild type cells. Transfected pools are plated at low density to allow for close-to-clonal outgrowth of stable expressing cells. The masterwells are screened for bispecific antibody expression and then scaled up in serum-free, suspension cultures to be used for production.

Clarified medium, into which the exemplified bispecific antibody has been secreted, is applied to a Protein A affinity column that has been equilibrated with a compatible buffer such as phosphate buffered saline (pH 7.4). The column is washed to remove nonspecific binding components. The bound bispecific antibody is eluted, for example, by pH gradient and neutralized for example with Tris, pH 8 buffer. Bispecific antibody fractions are detected, such as by SDS-PAGE or analytical size-exclusion, and then are pooled. Soluble aggregate and multimers may be effectively removed by common techniques including size exclusion, hydrophobic interaction, Capto multimodal chromatography, ion exchange, or hydroxyapatite chromatography. The bispecific antibody is concentrated and/or sterile filtered using common techniques. The purity of the exemplified bispecific antibody after these chromatography steps is greater than 98% (monomer). The bispecific antibody may be immediately frozen at −70° C. or stored at 4° C. for several months.

The relationship of the various regions and linkers comprising an exemplified bispecific antibody compound of the present invention, expressed and purified following procedures essentially as described above, is presented in Table 1 (numbering of amino acids applies linear numbering; assignment of amino acids to variable domains is based on the International Immunogenetics information System® available at www.imgt.org; assignment of amino acids to CDR domains is based on the well-known Kabat and North numbering conventions as reflected at the end of Table 1):

TABLE 1

Amino acid regions of an exemplified bispecific antibody of the present invention.

| SEQ ID NO: 1 | | | SEQ ID NO: 2 | | |
|---|---|---|---|---|---|
| | Region | Positions | | Region | Positions |
| Exemplified HCVR1 | FRH1-1 | 1-22 | Exemplified LCVR1 | FRL1-1 | 1-23 |
| | HCDR1 | 23-35 | | LCDR1 | 24-34 |

TABLE 1-continued

Amino acid regions of an exemplified bispecific antibody of the present invention.

| Dkk-1 | FRH1-2 | 36-49 | Dkk-1 | FRL1-2 | 35-48 |
|---|---|---|---|---|---|
| | HCDR2 | 50-66 | | LCDR2 | 49-56 |
| | FRH1-3 | 67-96 | | FRL1-3 | 57-88 |
| | HCDR3 | 97-108 | | LCDR3 | 89-97 |
| | FRH1-4 | 109-119 | | FRL1-4 | 98-107 |
| Exemplified Constant Region | CH | 120-445 | Exemplified Constant Region | CL | 108-214 |
| Exemplified Linker | L1 | 446-460 | | | |
| Exemplified HCVR2 RANKL | FRH2-1 | 461-482 | | | |
| | HCDR4 | 483-495 | | | |
| | FRH2-2 | 496-509 | | | |
| | HCDR5 | 510-526 | | | |
| | FRH2-3 | 527-556 | | | |
| | HCDR6 | 557-570 | | | |
| | FRH2-4 | 571-581 | | | |
| Exemplified Linker | L2 | 582-606 | | | |
| Exemplified LCVR2 RANKL | FRL2-1 | 607-629 | | | |
| | LCDR4 | 630-640 | | | |
| | FRL2-2 | 641-654 | | | |
| | LCDR5 | 655-662 | | | |
| | FRL2-3 | 663-694 | | | |
| | LCDR6 | 695-703 | | | |
| | FRL2-4 | 704-713 | | | |

| CDR | Starting Amino Acid Residue Defined By: | Ending Amino Acid Residue Defined By: |
|---|---|---|
| HCDR1 | North | Kabat |
| HCDR2 | Kabat | Kabat |
| HCDR3 | North | Kabat |
| HCDR4 | North | Kabat |
| HCDR5 | Kabat | Kabat |
| HCDR6 | North | Kabat |
| LCDR1 | Kabat | Kabat |
| LCDR2 | North | Kabat |
| LCDR3 | Kabat | Kabat |
| LCDR4 | Kabat | Kabat |
| LCDR5 | North | Kabat |
| LCDR6 | Kabat | Kabat |

The exemplified bispecific antibody compound presented in Table 1 comprises two first polypeptide chains having amino acid sequences of SEQ ID NO: 1 and two second polypeptide chains having amino acid sequences of SEQ ID NO: 2. According to the exemplified bispecific antibody compound, each of the first polypeptide chains forms an inter-chain disulfide bond with each of the second polypeptide chains between cysteine residue 133 of SEQ ID NO: 1 and cysteine residue 214 of SEQ ID NO: 2; at least two inter-chain disulfide bonds with the other first polypeptide chain, the first inter-chain disulfide bond forming between cysteine residue 225 (of SEQ ID NO: 1) of the first polypeptide chain and cysteine residue 225 (of SEQ ID NO: 1) of the other first polypeptide chain, the second inter-chain disulfide bond forming between cysteine residue 228 (of SEQ ID NO: 1) of the first polypeptide chain and cysteine residue 228 (of SEQ ID NO: 1) of the other first polypeptide chain; and an intra-chain disulfide bond formed in the scFV of each first polypeptide chain between cysteine residue 504 (of SEQ ID NO: 1) and cysteine residue 706 (of SEQ ID NO: 1) of each respective first polypeptide chain. Further, the exemplified bispecific antibody compound presented in Table 1 is glycosylated at asparagine residue 296 of SEQ ID NO: 1 of both first polypeptides.

Except as noted otherwise herein, the exemplified bispecific antibody compound referred to throughout the Examples refers to the exemplified bispecific antibody compound of the present invention presented in Table 1.

Bispecific Antibody Compound Solubility and Stability Analysis

The exemplified bispecific antibody compound is formulated in one of 10 mM citrate buffer pH 5.5 or 10 mM histidine buffer pH 5.5. The impact of 150 mM NaCl and 0.02% Tween80 added to the respective buffers is also evaluated. The bispecific antibody compound is concentrated in the respective buffer formulations to 1 mg/mL and 50 mg/mL using Amicon U.C. filters (Millipore, catalog # UFC903024).

Stability of the exemplified bispecific antibody compound is analyzed following incubation at 25° C. for 4 weeks. Percent high molecular weight (% HMW) is assessed with analytical size exclusion chromatography (aSEC) using a TSKgel Super SW3000 (Tosoh Bioscience product #18675) column. 50 mM sodium phosphate+350 mM NaCl, pH 7.0 is used as the mobile phase running at 0.4 mL/min for 15 minutes. A Volume of 5 μL (5 μg) of the concentrated bispecific antibody compound is injected into the column and the detection is measured at 214 nm. A volume of 1 μL (50 μg) is injected into the column and the detection is measured at 280 nm. Chromatograms are analyzed using ChemStation and % high molecular weight (HMW) is calculated using the ratio of AUC of the peaks eluted before the monomer peak to total AUC. These results are summarized in Table 2 (the addition of NaCl and Tween did not present any appreciable impact on results).

TABLE 2

Change in % HMW species from starting control over 4 weeks at 25° C., measured by aSEC.

| | % HMW Change | |
|---|---|---|
| Sample Conc. | Citrate Buffer | Histidine Buffer |
| 1 mg/mL (N = 1) | <0.4 | <0.4 |
| 50 mg/mL (N = 1) | 0.46-0.49 | 0.41-0.59 |

Solubility of the exemplified bispecific antibody compound is analyzed following incubation at 25° C. for one week. Solubility is assessed with bispecific antibody concentrated to 150 mg/mL (using Amicon U.C. filters, Millipore, catalog # UFC903024) and formulated in either 10 mM citrate at pH 5.5 including 150 mM NaCl or 10 mM histidine at pH 5.5 including 150 mM NaCl. The impact of 0.02% Tween80 added to the respective buffers is also evaluated. The exemplified bispecific antibody exhibited solubility of at least 148 mg/mL, within acceptable values for therapeutic bispecific antibodies (the addition of Tween did not present any appreciable impact on results). The exemplified bispecific antibody compound also lacked phase separation following the incubation period.

Viscosity of the exemplified bispecific antibody compound is analyzed at room temperature. Viscosity is assessed with bispecific antibody compound concentrated to 100 mg/mL (using Amicon U.C. filters, Millipore, catalog UFC903024) and formulated in either 10 mM citrate at pH 5.5 including 150 mM NaCl or 10 mM histidine at pH 5.5 including 150 mM NaCl. The exemplified bispecific antibody, when formulated in citrate exhibited a viscosity of 3.12 cP and when formulated in histidine exhibited a viscosity of 4.88 cP, within acceptable values for therapeutic bispecific antibodies.

Photostability analysis of the exemplified bispecific antibody compound is assessed with bispecific antibody concentrated at 50 mg/mL and formulated in 10 mM histidine, pH 5.5. Samples are exposed for 240000 lux hour visible light or 40 watt-hr/m² UV fight. Control ("dark") samples are not exposed to light. Samples are then analyzed on an aSEC column for change in % HMW compared to dark samples. When exposed to UV light no change in % HMW was recorded, when exposed to visible light a 1.62% HMW increase was recorded. Additionally, CDR oxidation and deamidation are not significantly increased by visible light exposure (2.8%) and UV exposure (0.8%). Photostability measures are all within acceptable values for therapeutic bispecific antibodies.

Freeze thaw analysis of exemplified bispecific antibody compound of the present invention is assessed following three freeze/thaw cycles performed according to Table 3:

TABLE 3

One Cycle of a Freeze Thaw Analysis.

| | Cycle Step | | | | | | | |
|---|---|---|---|---|---|---|---|---|
| | 1 | 2 | 3 | 4 | 5 | 6 | 7 | 8 |
| Target Temp. (° C.) | 5 | −1 | −30 | −70 | −30 | −1 | 0.5 | 15 |
| Temp. Rate (° C./min.) | 1 | 0.05 | 0.2 | 1 | 1 | 0.2 | 0.2 | 1 |
| Hold (min.) | 10 | 750 | 1 | 60 | 1 | 1000 | 1 | 1 |

Freeze/thaw analysis of the exemplified bispecific antibody compound is assessed with bispecific antibody compound concentrated at either 1 mg/mL or 50 mg/mL and formulated in either a.) 10 mM citrate, pH 5.5, with and without 0.02% Tween-80; or b.) 10 mM histidine, pH 5.5, with and without 0.02% Tween-80. Three freeze/thaw cycles (a single cycle represented in Table 3) are performed and particle growth for each sample is assessed using a HIAC Particle Counter (Pacific Scientific, p/n. 9703). Results are provided in Table 4.

TABLE 4

Particle Count Following Freeze/Thaw Analysis.

| | | Particle Count/mL | | | |
|---|---|---|---|---|---|
| | | (a) 10 mM histidine, pH 5.5 | | (b) 10 mM citrate, pH 5.5 | |
| Sample | Conc. | +Tween80 | −Tween80 | +Tween80 | −Tween80 |
| 0 Freeze/Thaw Cycles | 1 mg/mL (N = 1) | <1000 counts/mL | <1000 counts/mL | <1000 counts/mL | <1000 counts/mL |

TABLE 4-continued

Particle Count Following Freeze/Thaw Analysis.

| | | Particle Count/mL | | |
|---|---|---|---|---|
| | | (a) 10 mM histidine, pH 5.5 | | (b) 10 mM citrate, pH 5.5 |
| Sample | Conc. | +Tween80 | −Tween80 | +Tween80 | −Tween80 |
| 3 Freeze Thaw Cycles | 50 mg/mL (N = 1) | <1000 counts/mL | <1000 counts/mL | <1000 counts/mL | >1000 counts/mL |

The results provided in Table 4 demonstrate the exemplified bispecific antibody compound of the present invention, under both low and high concentration conditions, is stable following multiple freeze/thaw cycles.

The results provided herein demonstrate the exemplified bispecific antibody compound of the present invention, formulated as described herein, achieves high protein concentration solubility (greater than 150 mg/mL), displays less than a 0.5% HMW degradation, and possess viscosity and photostability within acceptable values for therapeutic bispecific antibodies.

Bispecific Antibody Binding Affinity to Dkk-1 and RANKL

Binding affinity and binding stoichiometry of the exemplified bispecific antibody to human Dkk-1 and human RANKL is determined using a surface plasmon resonance assay on a Biacore 2000 instrument primed with HBS-EP+ (10 mM Hepes, pH7.4+150 mM NaCl+3 mM EDTA+0.05% (w/v) surfactant P20) running buffer and analysis temperature set at 25° C. A CM5 chip (Biacore, pin. BR-100530) containing immobilized protein A (generated using standard NHS-EDC amine coupling) on all four flow cells (Fc) is used to employ a capture methodology. Antibody samples are prepared at 0.2-10 μg/mL by dilution into running buffer. Human Dkk-1 samples are prepared at final concentrations of 100 nM, 50 nM, 25 nM, 12.5 nM, 6.25 nM, 3.125 nM, 1.5625 nM, 0.78125 nM, 0.390625 nM, 0.1953125 nM, and 0 (blank) nM by dilution into running buffer. Human RANKL are prepared at final concentrations of 100 nM, 50 nM, 25 nM, 12.5 nM, 6.25 nM, 3.125 nM, 1.5625 nM, 0.78125 nM, 0.390625 nM, 0.1953125 nM, and 0 (blank) nM by dilution into running buffer.

Each analysis cycle consists of (1) capturing antibody samples on separate flow cells (Fc2 and Fc3); (2) injection of each human Dkk-1 concentration over all Fc at 50 μL/min for 300 seconds followed by return to buffer flow for 1200 seconds to monitor dissociation phase; (3) injection of each human RANKL concentration over all Fc at 100 μL/min for 150 seconds followed by return to buffer flow for 1800 seconds to monitor dissociation phase; (4) regeneration of chip surfaces with injection of 10 mM glycine, pH 1.5, for 120 seconds at 5 μL/min over all cells; and (5) equilibration of chip surfaces with a 10 μL (60-sec) injection of HBS-EP+. Data are processed using standard double-referencing and fit to a 1:1 binding model using Biacore 2000 Evaluation software, version 2.0.3, to determine the association rate ($k_{on}$, $M^{-1}$ $s^{-1}$ units), dissociation rate ($k_{off}$, $s^{-1}$ units), and $R_{max}$ (RU units). The equilibrium dissociation constant ($K_D$) is calculated from the relationship $K_D=k_{off}/k_{on}$, and is in molar units. Results are provided in Table 5.

TABLE 5

Binding affinity to human Dkk-1 and human RANKL by the exemplified bispecific antibody at 37° C.

| Antigen | $k_{on}$ Avg ($10^5$ $M^{-1}s^{-1}$) | $k_{off}$ Avg $s^{-1}$ ($10^{-6}$) | $K_D$ Avg pM | n |
|---|---|---|---|---|
| Human RANKL | 5.3 | 4.2 | 87.4 | 5 |
| Human Dkk-1 | 18.3 | 6.55 | 35.7 | 3 |

The results provided in Table 5 demonstrate that the exemplified bispecific antibody of the present invention binds human RANKL and human Dkk-1 with high affinity at 25° C.

Neutralization of Dkk-1 induced Reduction in Luciferase Activity in Vitro

Murine preosteoblastic MC3T3E1/Topflash cells which have been stably infected with TCF/LEF luciferase reporter are used to assess the ability of the exemplified bispecific antibody presented in Table 1 to neutralize Dkk-1 activity. Wnt3a induces TCF/LEF-regulated luciferase luminescence. Human Dkk-1 blocks Wnt3a-induced TCF/LEF luciferase expression. Neutralization of Dkk-1 activity by the exemplified bispecific antibody is measured through quantification of luciferase luminescence restoration.

MC3T3E1 cells are routinely cultured under selective pressure of 1.25 μg/ml puromycin in MEMα media (Gibco, p/n A10490-01) containing 10% FBS (Gihco, p/n 10082-147) and 1× penicillin/streptomycin (Hyclone, p/n.SV30010). 40,000 MC3T3E1 cells per well (in 100 μL) are added to the wells of 96 well tissue culture plates (Costar, p/n.3903). The cells are incubated overnight at 37° C. (under 5% $CO_2$ and 95% humidity).

Wnt3a (R&D, p/n.5036-WN) is diluted to 0.33 ug/mL and recombinant hDkk-1 is diluted to 1 ug/ml in growth media. Growth media supplemented with Wnt3a and hDkk-1 (at the respective concentrations) is used to prepare dose ranges of 300 nM to 1.23 nM for: a.) exemplified bispecific antibody; b.) a Dkk-1 neutralizing antibody (a Dkk-1 antibody having an IgG4 backbone and the same heavy and light chain variable region sequences as the mAb portion of the exemplified bispecific antibody); and c.) a RANKL neutralizing antibody (an IgG4 RANKL mAb having the same CDR sequences as the scFv portion of the exemplified bispecific antibody). Growth media is used for "media only" and "media with Wnt3a" controls.

Following overnight incubation, media is removed and cells are treated with respective antibody treatment concentration or control as described above (in duplicate). Cells are then incubated for 3 hours and 30 minutes at 37° C. followed by incubation for 30 minutes at room temperature. Following incubation, treatments are removed from the cells and 50 μL of Glo Lysis Buffer (Promega, p/n E266A) is added to the cells. Cells are then lysed with gentle agitation on a plate shaker for between 5 to 10 minutes. Following cell lysis, 50 µL premixed Bright Glo Luciferase Reagent (Promega, p/n.E620) is added and luminescence is measured on a Wallac Victor 1420 Multilabel Plate Reader. $EC_{50}$ values and confidence intervals (CI) for all treatment groups are calculated using a four-parameter logistic regression model with GraphPad Prism 6.

The results demonstrate that the exemplified bispecific antibody of the present invention neutralizes human Dkk-1 blocking of Wnt3a-induced TCF/LEF luciferase activity. The inhibition is comparable to that observed with the positive control Dkk-1 antibody (with a mean $EC_{50}$ for the exemplified bispecific antibody of 5.30 nM (CI=4.12–6.82 nM) nM versus 6.61 (CI=4.92–8.86 nM) for the positive control Dkk-1 antibody). The RANKL antibody and media controls do not neutralize human Dkk-1 from blocking Wnt3a-induced TCF/LEF luciferase in the MC3T3E1. cells at any concentration tested. The results demonstrate the exemplified bispecific antibody of the present invention effectively neutralizes Dkk-1.

Neutralization of RANKL-Induced NE-kB-Driven Luciferase Activity in Vitro

HEK293 cells, which stably co-express human RANK and a NF-kB driven luciferase reporter, are used to assess the ability of the exemplified bispecific antibody presented in Table 1 to neutralize RANKL activity. In the above-described HEK293 cell model, RANK, when bound by human RANKL, induces NF-kB signaling resulting in luciferase luminescence. Neutralization of RANKL binding to RANK, by the exemplified bispecific antibody, is measured by a reduction of luciferase luminescence.

HEK293 cells are routinely cultured under selective pressure of 700 µg/mL Geneticin (HyClone, p/n.SV30069.01). 25,000 cells/well are added to the wells of 96 well tissue culture plates (Benton Dickinson, p/n.354620) in assay media (50 µL DMEM/F12 (1:3) media (Gibco, p/n.930152DK) containing 5% FBS (Gibco, p/n.10082-147), 20 nM Hepes (HyClone, p/n.SH30237.01), 1×Gluta-Max (Gibco, p/n.35050-61) and 1× penicillin/streptomycin (Hyclone, p/n.SV30010)). Cells are incubated at 37° C. (with 5% $CO_2$ and 95% humidity) overnight.

Assay media including 100 ng/mL of hRANKL are used to prepare dose ranges of 100 nM to 0.005 nM (with 1:3 serial dilutions) for each of: a.) the exemplified bispecific antibody and b.) a RANKL neutralizing antibody (an IgG4 RANKL mAb having the same CDR sequences as the scFv portion of the exemplified bispecific antibody). Assay medium is used for "media only" and "media with 100 ng/ml RANKL" controls. All treatment groups are incubated for 30 minutes at room temperature before being added to cells.

Following overnight incubation of the cells, existing growth media is removed. Cells are resuspended in 50 µL of one of the respective antibody treatments triplicate) at one of the above concentrations or in a growth media control. Cells are incubated for 18 hours at 37° C. (under 5% CO2 and 95% humidity). Following incubation, growth media is removed from the cells and cells are suspended in 50 µL of BugLite (2.296 g DTT (Sigma, p/n.D0632), 1.152 g Coenzyme A (Sigma, p/n. C-3019), 0.248 g ATP (Sigma, p/n.A7699) in 1 L 1% Trition X-100 Lysis Buffer (30 mL Triton X-100 (Fisher, p/n.BP151-500), 3 mL MgCl (Sigma, p/n.M9272), 108.15 mL 1M Trizma HCL (Sigma, p/n.T-3253), 41.85 mL 1M Trizma Base (Sigma, p/n.T-1503) and 817 mL H2O)). Cells are then lysed with gentle agitation on a plate shaker for between 5 to 10 minutes. Following cell lysis, luminescence is measured on a Wallac. Victor 1420 Multilabel Plate Reader. $IC_{50}$ values for all treatment groups are calculated using a three-parameter logistic regression model with GraphPad Prism 6.

The results demonstrate that the exemplified bispecific antibody of the present invention neutralized human RANKL induced NF-kB driven luciferase luminescence. The inhibition was comparable to that observed with the positive control RANKL antibody (with a mean $IC_{50}$ for the exemplified bispecific antibody of 1.20 nM versus 1.30 nM for the positive control RANKL antibody). Media controls did not neutralize human RANKL induced NF-kB driven luciferase luminescence in the HEK293 cell model at any concentration tested. These results demonstrate the exemplified bispecific antibody of the present invention effectively neutralizes RANKL.

In Vivo Efficacy Analysis in Cortical Defect Model

Systemic effects on bone and vertebrae healing, in vivo, are assessed using a rodent cortical defect model. Fourteen week old male athymic nude rats (Harlan, Indianapolis, Ind.) are maintained on a 12 hour light/dark cycle at 22° C. with ad lib access to food (TD 89222 with 0.5% Ca. and 0.4% P, Teklad, Madison, Wis.) and water.

Cortical defect surgery is performed on the mice, essentially as described in Komatsu, et al. (Endocrinology, 150: 1570-1579, 2009). Briefly, on day 0.2 mm diameter holes extending though both the anterior and posterior cortices are drilled through the diaphysis of the left and right femurs. On day 1 post-surgery, mice are divided into 7 groups and given a single intraperitoneal injection of one of: a.) 1.4 mg/kg exemplified bispecific antibody (N=9), b.) 4.2 mg/kg exemplified bispecific antibody (N=9); c.) 14 mg/kg exemplified bispecific antibody (N=9), d.) 42 mg/kg exemplified bispecific antibody (N=9); e.) 3 mg/kg Dkk-1 assay control antibody (an IgG4 Dkk-1 mAb having the same heavy and light chain variable region sequences as the mAb portion of the exemplified bispecific antibody)(N=9); f.) 3 mg/kg RANKL assay control antibody (an IgG4 RANKL mAb having the same CDR sequences as the scFv portion of the exemplified bispecific antibody) (N=9), and g.) 3 mg/kg human IgG4 negative control antibody (N=9). On day 35 mice are sacrificed.

At days 7, 21 and 35, post-surgery, whole femur bone mass density (BMD) is monitored longitudinally in vivo by quantitative computed tomography (qCT) using GE Locus Ultra CT Scanner (GE Healthcare, London, Ontario, Canada). Results are provided in Table 6. Similarly, at days 7, 21 and 35, post-surgery, BMD is monitored for lumbar vertebrae 5 (LV5) by qCT. Results are provided in Table 7 (data presented as mean±SE. Dunnett's T test).

TABLE 6

BMD Analysis at Cortical Defect Site.

| | BMD at Cortical Defect Site ($mg/cm^3$) | | |
|---|---|---|---|
| | Day 7 | Day 21 | Day 35 |
| IgG4 Control Ab (3 mg/kg) | 387 ± 6 | 441 ± 6 | 529 ± 10 |
| Exemplified Bispecific Ab (1.4 mg/kg) | 371 ± 5 | 476 ± 16 | 599 ± 17 |
| Exemplified Bispecific Ab (4.2 mg/kg) | 363 ± 7 | 504 ± 10 | 676 ± 17 |
| Exemplified Bispecific Ab (14 mg/kg) | 374 ± 8 | 519 ± 14 | 708 ± 16 |
| Exemplified Bispecific Ab (42 mg/kg) | 375 ± 5 | 504 ± 12 | 686 ± 31 |

The results presented in Table 6 demonstrate that a single dose (of 4.2 mg/kg or higher) of the exemplified bispecific antibody of the present invention increases the BMD at the cortical defect as early as day 21 post surgery as compared to IgG4 control antibody treated rats.

TABLE 7

BMD Analysis of LV5.

|  | % BMD Change of LV5 as Compared to Day 7 | |
|---|---|---|
|  | Day 21 | Day 35 |
| IgG4 Control Ab (3 mg/kg) | −0.49 ± 0.81 | 1.24 ± 0.61 |
| Exemplified Bispecific Ab (1.4 mg/kg) | 1.90 ± 0.58 | 3.73 ± 0.94 |
| Exemplified Bispecific Ab (4.2 mg/kg) | 3.01 ± 0.38 | 4.54 ± 0.53 |
| Exemplified Bispecific Ab (14 mg/kg) | 4.59 ± 0.80 | 7.17 ± 0.76 |
| Exemplified Bispecific Ab (42 mg/kg) | 4.73 ± 1.77 | 5.02 ± 1.46 |

The results presented in Table 7 demonstrate that a single dose of the exemplified bispecific antibody of the present invention increases the BMD at LV5 as early as day 21 post surgery as compared to IgG4 control antibody treated rats.

Post-sacrifice, femoral biomechanical load-to-failure analysis, femoral neck stiffness, and vertebral load-to-failure analysis is performed. Femoral biomechanical load-to-failure strength and femoral neck stiffness are analyzed by mounting the proximal half of the femur vertically in a chuck at room temperature and applying a downward force to the femoral head until failure. Vertebrae (LV5) are load-to-failure tested in compression tests using a MTS model 1/S materials testing device and analyzing with TestWorks 4 software (MTS Corp.). Ultimate load is measured as the maximal force sustained by the vertebrae. Results are provided in Table 8.

TABLE 8

Femoral Stiffness; Femoral Neck Strength; and Vertebral Strength Analysis (Mean ± Std. Dev.).

|  | Femoral Stiffness at the Cortical Defect Site (newtons/mm) | Femoral Strength (newtons) | Vertebral Strength (newtons) |
|---|---|---|---|
| IgG4 Control Ab (3 mg/kg) | 244 ± 9 | 83.1 ± 3.7 | 222 ± 36 |
| Exemplified Bispecific Ab (1.4 mg/kg) | 282 ± 16 | 92.2 ± 2.2 | 321 ± 15 |
| Exemplified Bispecific Ab (4.2 mg/kg) | 294 ± 16 | 102.4 ± 2.3 | 323 ± 19 |
| Exemplified Bispecific Ab (14 mg/kg) | 330 ± 25 | 97.7 ± 2.4 | 335 ± 24 |
| Exemplified Bispecific Ab (42 mg/kg) | 346 ± 23 | 97.5 ± 2.7 | 339 ± 25 |

The results presented in Table 8 demonstrate that a single dose of the exemplified bispecific antibody of the present invention increases the femoral stiffness and femoral neck strength as well as vertebral strength as compared to IgG4 control antibody treated rats.

Osseous Integration Analysis in Vivo

Osseous integration and implant fixation, as well as systemic effects on vertebrae healing, are assessed in vivo using a rodent tibia screw implant model. Twenty-three week old male Sprague-Dawley rats (Charles River Labs., Int'l Inc.) undergo surgical implantation of a titanium screw (2×4 mm) into the medial lateral side in both hind leg tibiae. One day post-surgery (day 1). rats are divided into 5 groups and given a subcutaneous injection of one of: a.) 3 mg/kg IgG4 negative control antibody (N=9); b.) 3 mg/kg Dkk-1 assay control antibody (an IgG4 Dkk-1 mAb having the same heavy and light chain variable region sequences as the mAb portion of the exemplified bispecific antibody)(N=9); c.) 3 mg/kg RANKL assay control antibody (an IgG4 RANKL mAb having the same CDR sequences as the scFv portion of the exemplified bispecific antibody) (N=9); d.) 4.2 mg/kg exemplified bispecific antibody (N=9); e.) 14 mg/kg exemplified bispecific antibody (N=9); and f.) 4.2 mg/kg exemplified bispecific antibody at both days 1 and 8 (N=9). On day 21 rats are sacrificed.

After sacrifice, both tibiae are removed from each rat, cleaned and fixed in a 50/50 ethanol/saline solution. A biomechanical pull-to-failure force test (at a speed of 10 mm/min) is performed on each tibia ex vivo using an industrial digital force gauge (Mark-10, Model M3-50, ESM301, Indiana). Additionally, Bone Mineral Content (BMC) change at L5 is also assessed in rats with μCT for assessment of systemic effect. Results of implant pull-to-failure force assessment are provided in Table 9 (data presented as mean±SE, Dunnett's T test). Results of BMC change at L5 are provided in Table 10 (data presented as mean±SE, Dunnett's T test).

TABLE 9

Implant Pull-to-Failure Force Analysis.

| Study Compound | Day(s) of Administration | Implant Pull-to-Failure Force (N) |
|---|---|---|
| IgG4 Control Ab (3 mg/kg) | 1 | 93.0 ± 4.2 |
| Exemplified Bispecific Ab (4.2 mg/kg) | 1 | 105.1 ± 5.1 |
| Exemplified Bispecific Ab (14 mg/kg) | 1 | 117.0 ± 6.2 |
| Exemplified Bispecific Ab (4.2 mg/kg) | 1, 8 | 122.1 ± 9.5 |

The results presented in Table 9 demonstrates that both a single and multiple dose(s) of the exemplified bispecific antibody presented in Table 1 increases the implant pull-to-failure force in a concentration (and frequency) dependent manner as compared to IgG4 control antibody treated rats. This data supports a finding that the exemplified bispecific antibody enhances osseous integration and implant fixation.

TABLE 10

BMC Change Analysis of L5.

| Study Compound | Day(s) of Administration | BMC Change (mg) |
|---|---|---|
| IgG4 Control Ab (3 mg/kg) | 1 | 1.231 ± 0.025 |
| Exemplified Bispecific Ab (4.2 mg/kg) | 1 | 1.314 ± 0.022 |
| Exemplified Bispecific Ab (14 mg/kg) | 1 | 1.312 ± 0.046 |
| Exemplified Bispecific Ab (4.2 mg/kg) | 1, 8 | 1.336 ± 0.0312 |

The results presented in Table 10 demonstrates that a single dose of a bispecific antibody of the present invention demonstrates a systemic effect improving BMC of L5 following tibial implant as compared to IgG4 control antibody treated rats.

In Vivo Efficacy Analysis in Posterior Lumbar Fusion Model

Systemic effects on bone and vertebrae healing in spinal fusion models, in vivo, are assessed using a rodent posterior lumbar fusion model. Fourteen week old male Sprague-Dawley rats (Charles River Labs., Int'l Inc.), having mass of between 450-530 g, undergo left iliac crest surgery for harvesting a bone autograft of 0.5×0.5 cm. The bone graft is immediately transplanted to decorticated lumbar vertebrae 5 and 6 (L5 and L6) transverse processes in the same rat from which the graft was harvested. In a first study (Study 1), a total of 48 rats undergo transplant surgery; in a second study (Study 2) a total of 60 rats undergo transplant surgery. On the day of surgery (day 0) digital radiographs are taken to ensure graft positioning.

Day 3 post-surgery the Study 1 transplant group rats are divided into 4 groups and given a single subcutaneous injection of one of: a.) 5 mg/kg IgG4 negative control antibody (N=12); b.) 5 mg/kg Dkk-1 assay control antibody (an IgG4 Dkk-1 mAb having the same heavy and light chain variable region sequences as the mAb portion of the exemplified bispecific antibody) (N=12); c.) 5 mg/kg RANKL assay control antibody (an IgG4 RANKL mAb having the same CDR sequences as the scFv portion of the exemplified bispecific antibody) (N=12); and d.) 7.2 mg/kg Dkk-1/RANKL bispecific antibody (slightly varied from the exemplified bispecific antibody of Table 1 at L1, L2, and framework amino acid sequences for HCVR2 and LCVR2) (N=12). On day 28 rats are sacrificed.

Day 3 post-surgery the Study 2 transplant group rats are divided into 5 groups and given a single subcutaneous injection of one of: a.) 1 mg/kg IgG4 negative control antibody (N=12); b.) 1 mg/kg Dkk-1 assay control antibody (an IgG4 Dkk-1 mAb having the same heavy and light chain variable region sequences as the mAb portion of the exemplified bispecific antibody) (N=12); c.) 1 mg/kg RANKL assay control antibody (an IgG4 RANKL mAb having the same CDR sequences as the scFv portion of the exemplified bispecific antibody) (N=12); d.) 1.4 mg/kg Dkk-1/RANKL bispecific antibody (slightly varied from the exemplified bispecific antibody of Table 1 at L1, L:2, and framework amino acid sequences for HCVR2 and LCVR2) (N=12); and e.) 7.2 mg/kg Dkk-1/RANKL bispecific antibody (slightly varied from the exemplified bispecific antibody of Table 1 at L1, L2. and framework amino acid sequences for HCVR2 and LCVR2) (N=12). On day 28 rats are sacrificed.

After sacrifice, all rats are assessed for spinal fusion rate and quality. Study 1 transplant group rats are assessed for BMD change, with µCT, at lumbar vertebrae 3 (L3, non-transplant vertebrae) to assess systemic bone effect. Spinal fusion rate and quality is evaluated using 3D micro CT images (µCT40) with a resolution of 36 µm per voxel. The 3D images obtained are used to assess osseous tissue fusion using a scoring system: 0=no fusion; 3=partial fusion; and 5=full fusion, where fusion rate is the percentage of combined partial and full fusion scores in each group. Results of spinal fusion rate and quality (at L5 and L6) are provided in Table 11 (data presented as mean score±SE, Fisher exact test). Results of BMD change at L3 (in Study 1 transplant group) are provided in Table 12 (data presented as mean SE, Dunnett's T test).

TABLE 11

Spinal Fusion Rate and Quality Analysis in Posterior Lumbar Fusion Model.

| Transplant Group | Study Compound | Fusion Rate (%) | Fusion Quality (avg. score) |
|---|---|---|---|
| Study 1 | IgG4 Control Ab (5 mg/kg) | 58 | 2.50 ± 1.51 |
|  | Dkk-1/RANKL Bispecific Ab (7.2 mg/kg) | 100 | 3.83 ± 1.03 |
| Study 2 | IgG4 Control Ab (1 mg/kg) | 50 | 2.40 ± 1.56 |
|  | Dkk-1/RANKL Bispecific Ab (1.4 mg/kg) | 92 | 3.30 ± 1.15 |
|  | Dkk-1/RANKL Bispecific Ab (7.2 mg/kg) | 82 | 410 ± 1.64 |

The results presented in Table 11 demonstrates that a single dose of a bispecific antibody of the present invention increases the fusion rate and quality at posterior lumbar fusion sites as early as day 28 days post-surgery as compared to IgG4 control antibody treated rats.

TABLE 12

BMD Change Analysis of Adjacent Bone in Posterior Lumbar Fusion Model.

| Transplant Group | Study Compound | BMD Change (mg/cm$^3$) |
|---|---|---|
| Study 1 | IgG4 Control Ab (5 mg/kg) | 461.73 ± 13.08 |
|  | Dkk-1/RANKL Bispecific Ab (7.2 mg/kg) | 510.46 ± 6.04 |

The results presented in Table 12 demonstrates that a single dose of a bispecific antibody of the present invention demonstrates a systemic effect improving BMD of adjacent vertebrae bone following a posterior lumbar fusion procedure as early as day 28 days post-surgery as compared to IgG4 control antibody treated rats.

```
                        Sequences

SEQ ID NO: 1 - Exemplified First Polypeptide
(of exemplified bispecific antibody compound
of Table 1)
EVQLVESGGGLVQPGGSLRLSCAASGFTFSSYTMSWVRQAPGKGLEW

VATISGGGFGTYYPDSVKGRFTISRDNAKNSLYLQMNSLRAEDTAVY

YCARPGYNNYYFDIWGQGTTVTVSSASTKGPSVFPLAPCSRSTSEST

AALGCLVKDYFPEPVTVSWNSGALTSGVHTFPAVLQSSGLYSLSSVV

TVPSSSLGTKTYTCNVDHKPSNTKVDKRVESKYGPPCPPCPAPEAAG

GPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPS

SIEKTISKAKGQPREPQVYTLPPSQEEMTKNQVSLTCLVKGFYPSDI

AVEWESNGQPENNYKTTPPVLDSDGSFFLYSRLTVDKSRWQEGNVFS

CSVMHEALHNHYTQKSLSLSLGGGGSGGGGSGGGGSQVQLVQSGAE

VKKPGSSVKVSCKASGYAFTNYYIEWVRQAPGQCLEWMGVINPGWGD

TNYNEKFKGRVTITADKSTSTAYMELSSLRSEDTAVYYCARRDTAHG

YYALDPWGQGTTVTVSSGGGGSGGGGSGGGGSGGGGSGGGGSDIQMT

QSPSSLSASVGDRVTITCKASQNVGTNVAWYQQKPGKAPKLLIYSAS
```

| Sequences |
| --- |
| YRYSGVPSRFSGSGSGTDFTLTISSLQPEDFATYYCQQYWDYPLTFG |
| CGTKVEIK |
| SEQ ID NO: 2 - Exemplified Second Polypeptide (of the exemplified bispecific antibody compound of Table 1)<br>EIVLTQSPATLSLSPGERATLSCHASDSISNSLHWYQQKPGQAPRLL |
| IYYARQSIQGIPARFSGSGSGTDFTLTISSLEPEDFAVYYCQQSESW |
| PLHFGGGTKVEIKRTVAAPSVFIFPPSDEQLKSGTASVVCLLNNFYP |
| REAKVQWKVDNALQSGNSQESVTEQDSKDSTYSLSSTLTLSKADYEK |
| HKVYACEVTHQGLSSPVTKSFNRGEC |
| SEQ ID NO: 3 - DNA Seq. Encoding the Exemplified First Polypeptide (SEQ ID NO. 1) and a Signal Peptide<br>atggagacggacactctcctcctgtgggtattgctcctttgggtccc |
| tggttctacaggggaggtacagctggtagaaagcggtgggggattgg |
| tacaaccaggtggatctctccggttgtcatgtgcagctagtgggttt |
| accttctccagttatacgatgtcttgggtgagacaagcgcccggtaa |
| aggattggagtgggtcgcaaccatcagtggaggagggtttggaacat |
| actaccctgatagcgttaaggggcggtttaccataagcagagataac |
| gcgaagaactctctctaccttcaaatgaactctctgcgggctgaaga |
| tacagctgtgtattattgcgcccgccctgggtataacaattactact |
| tcgatatttggggccaaggacaaccgtaaccgtgtctagcgcttca |
| actaagggtccaagcgtgttcccttttggcaccctgcagcagaagcac |
| gtccgagtctaccgctgctttgggctgtctcgtcaaggactacttcc |
| ccgaaccagttactgttcttggaactctggtgcactcacaagtggg |
| gtccatacgttccccgccgttttgcaatccagcgggttgtactctct |
| ttcatccgtggtcactgttcctagctccagcctcggcactaaaactt |
| acacttgtaatgtagaccataagcccagcaacaccaaggtggataag |
| agagtcgagtccaagtacgccctccttgtcctccatgtcctgcgcc |
| ggaggccgccggaggaccttctgtgttcctttttccaccaaaaccta |
| aagacacccttatgatatcccgaactcccgaggtaacgtgcgtggta |
| gtcgatgtaagccaggaagatcccgaagtccagttcaattggtacgt |
| tgacggcgtcgaagtccacaatgctaagacaaaacccagggaagagc |
| agttcaacagcacctatcgcgtagtgagcgtactgaccgtgcttcac |
| caagactggctcaacggtaaggaatataaatgtaaggtttccaataa |
| aggcctgcccagctcaattgagaaaaccatatccaaagctaagggg |
| aacctcgagaaccacaggtttacacacttcctccatcacaggaggaa |
| atgacgaaaaatcaggttagcctgacttgtctcgttaaaggatttta |
| tccatctgatattgccgtagaatgggagagtaatggacagcctgaga |
| ataactataagaccacaccaccccgtcctcgactctgacggctcattc |
| ttcctgtattctcgcttgacggtggacaagagcagatggcaggaagg |
| gaacgtgttttcttgcagtgtgatgcacgaggcactgcataatcatt |

| Sequences |
| --- |
| acacacagaagtctttgtccctgtcactgggtggcggaggaggttca |
| ggaggtgggggcagtggcggcggaggctcacaggtccagcttgtcca |
| gtctggggcagaggtgaagaagcccggagtagtgtgaaggtcagct |
| gtaaggcgtcagggtacgcttttactaattactacattgaatgggtg |
| agacaggctccaggccagtgtcttgagtggatgggcgtgattaatcc |
| aggctggggtgacactaattacaatgagaagttcaaagggcgggtga |
| ctatcacggcagataagtctacttccactgcttatatggagctctcc |
| tccctgaggagcgaagacaccgctgtttattattgtgcccggcgaga |
| tacagcccatgggtattatgccctcgatccatggggccagggcacga |
| cagttaccgtgagctccggaggagggagcggggcggggatct |
| ggaggaggaggaagtggaggtggagggtctgggggaggcggaagcga |
| tatccagatgactcaaagccctagttccttgagcgcctctgtgggcg |
| acagagtgacaataacctgtaaagcatcacaaaacgtgggcaccaac |
| gtggcgtggtatcaacaaaaacctggcaaggcgcctaagttgctgat |
| ttatagtgcatcttacaggtattcaggggtgccctccagatttagtg |
| gcagtggcagcggaaccgatttcactctcacaataagctctcttcag |
| ccagaggacttcgcgacgtattattgccaacagtattgggactatcc |
| actgactttcggttgtggaacaaaggttgagatcaag |
| SEQ ID NO: 4 - DNA Seq. Encoding the Exemplified Second Polypeptide (SEQ ID NO. 2) and a Signal Peptide<br>atggagacagacacactcctgctatgggtactgctgctctgggttcc |
| aggatccactggtgaaattgtgttgacacagtctccagccaccctgt |
| ctttgtctccaggggaaagagccaccctctcctgccacgccagcgac |
| agtattagcaacagcctacactggtaccaacagaaacctggccaggc |
| tcccaggctcctcatctattatgctagacagtccatccagggcatcc |
| cagccaggttcagtggcagtgggtctgggacagacttcactctcacc |
| atcagcagcctagagcctgaagattttgcagtttattactgtcaaca |
| gagtgagagctggccgctccacttcggcggagggaccaaggtggaga |
| tcaaacgaactgtggctgcaccatctgtcttcatcttcccgccatct |
| gatgagcagttgaaatctggaactgcctctgttgtgtgcctgctgaa |
| taacttctatcccagagaggccaaagtacagtggaaggtggataacg |
| ccctccaatcgggtaactcccaggagagtgtcacagagcaggacagc |
| aaggacagcacctacagcctcagcagcaccctgacgctgagcaaagc |
| agactacgagaaacacaaagtctacgcctgcgaagtcacccatcagg |
| gcctgagctcgcccgtcacaaagagcttcaacaggggagagtgc |
| SEQ ID NO: 5 - Exemplified HCVR1 (of exemplified bispecific antibody compound of Table 1)<br>EVQLVESGGGLVQPGGSLRLSCAASGFTFSSYTMSWVRQAPGKGLEW |
| VATISGGGFGTYYPDSVKGRFTISRDNAKNSLYLQMNSLRAEDTAVY |
| YCARPGYNNYYFDIWGQGTTVTVSS |

| Sequences |
|---|
| SEQ ID NO: 6 - Exemplified HCVR2 (of exemplified bispecific antibody compound of Table 1)<br>QVQLVQSGAEVKKPGSSVKVSCKASGYAFTNYYIEWVRQAPGQCLEW<br>MGVINPGWGDTNYNEKFKGRVTITADKSTSTAYMELSSLRSEDTAVY<br>YCARRDTAHGYYALDPWGQGTTVTVSS |
| SEQ ID NO: 7 - Exemplified LCVR1 (of exemplified bispecific antibody compound of Table 1)<br>EIVLTQSPATLSLSPGERATLSCHASDSISNSLHWYQQKPGQAPRLL<br>IYYARQSIQGIPARFSGSGSGTDFTLTISSLEPEDFAVYYCQQSESW<br>PLHFGGGTKVEIK |
| SEQ ID NO: 8 - Exemplified LCVR2 (of exemplified bispecific antibody compound of Table 1)<br>DIQMTQSPSSLSASVGDRVTITCKASQNVGTNVAWYQQKPGKAPKLL<br>IYSASYRYSGVPSRFSGSGSGTDFTLTISSLQPEDFATYYCQQYWDY<br>PLTFGCGTKVEIK |
| SEQ ID NO: 9 - Exemplified HCDR1 (of exemplified bispecific antibody compound of Table 1)<br>AASGFTFSSYTMS |
| SEQ ID NO: 10 - Exemplified HCDR2 (of exemplified bispecific antibody compound of Table 1)<br>TISGGGFGTYYPDSVKG |
| SEQ ID NO: 11 - Exemplified HCDR3 (of exemplified bispecific antibody compound of Table 1)<br>ARPGYNNYYFDI |
| SEQ ID NO: 12 - Exemplified HCDR4 (of exemplified bispecific antibody compound of Table 1)<br>KASGYAFTNYYIE |
| SEQ ID NO: 13 - Exemplified HCDR5 (of exemplified bispecific antibody compound of Table 1)<br>VINPGWGDTNYNEKFKG |
| SEQ ID NO: 14 - Exemplified HCDR6 (of exemplified bispecific antibody compound of Table 1)<br>ARRDTAHGYYALDP |
| SEQ ID NO: 15 - Exemplified LCDR1 (of exemplified bispecific antibody compound of Table 1)<br>HASDSISNSLH |
| SEQ ID NO: 16 - Exemplified LCDR2 (of exemplified bispecific antibody compound of Table 1)<br>YYARQSIQ |
| SEQ ID NO: 17 - Exemplified LCDR3 (of exemplified bispecific antibody compound of Table 1)<br>QQSESWPLH |
| SEQ ID NO: 18 - Exemplified LCDR4 (of exemplified bispecific antibody compound of Table 1)<br>KASQNVGTNVA |
| SEQ ID NO: 19 - Exemplified LCDR5 (of exemplified bispecific antibody compound of Table 1)<br>YSASYRYS |
| SEQ ID NO: 20 - Exemplified LCDR6 (of exemplified bispecific antibody compound of Table 1)<br>QQYWDYPLT |
| SEQ ID NO: 21 - Exemplified L1 of the exemplified bispecific antibody compound of Table 1<br>GGGGSGGGGSGGGGS |
| SEQ ID NO: 22 - Exemplified L2 of the exemplified bispecific antibody compound of Table 1<br>GGGGSGGGGSGGGGSGGGGSGGGGS |

We claim:

1. A bispecific antibody compound that binds DKK-1 and RANKL comprising two first polypeptide chains and two second polypeptide chains wherein each of, a.) said first polypeptide chain comprises a single chain variable fragment (scFv) and a mAb IgG heavy chain (HC), the HC having a heavy chain variable region (HCVR1) comprising heavy chain CDRs (HCDR) 1-3 wherein the amino acid sequence of HCDR1 is SEQ ID NO:9, the amino acid sequence of HCDR2 is SEQ ID NO:10, the amino acid sequence of HCDR3 is SEQ ID NO:11, and the scFv having a heavy chain variable region (HCVR2) and a light chain variable region (LCVR2), HCVR2 comprising HCDRs 4-6 and LCVR2 comprising LCDRs 4-6, wherein the amino acid sequence of HCDR4 is SEQ ID NO:12, the amino acid sequence of HCDR5 is SEQ ID NO:13, the amino acid sequence of HCDR6 is SEQ ID NO:14, the amino acid sequence of LCDR4 is SEQ ID NO:18, the amino acid sequence of LCDR5 is SEQ ID NO:19, and the amino acid sequence of LCDR6 is SEQ ID NO:20; and b.) said second polypeptide comprises a mAb light chain (LC) having a LCVR1 comprising light chain CDRs (LCDR) 1-3, wherein the amino acid sequence of LCDR1 is SEQ ID NO:15, the amino acid sequence of LCDR2 is SEQ ID NO:16, the amino acid sequence of LCDR3 is SEQ ID NO:17, wherein each scFv is independently linked to said HC via polypeptide linker (L1) covalently attached to the N-terminus of HCVR2 and the C-terminus of HC, and LCVR2 is linked to HCVR2 of the same scFv via a second polypeptide linker (L2) covalently attached to the N-terminus of LCVR2 and the C-terminus of HCVR2.

2. The bispecific antibody compound of claim 1, wherein the amino acid sequence of HCVR1 is SEQ ID NO:5, the amino acid sequence of LCVR1 is SEQ ID NO:7, the amino acid sequence of HCVR2 is SEQ ID NO:6, and the amino acid sequence of LCVR2 is SEQ ID NO:8.

3. The bispecific antibody compound of claim 2, wherein the amino acid sequence of L1 is SEQ ID NO: 21 and the amino acid sequence of L2 is SEQ ID NO: 22.

4. A bispecific antibody compound comprising two first polypeptide chains and two second polypeptide chains wherein the amino acid sequence of each of the first polypeptides is SEQ ID NO:1 and the amino acid sequence of each of the second polypeptides is SEQ ID NO:2.

5. A pharmaceutical composition comprising a bispecific antibody compound that binds DKK-1 and RANKL and one or more pharmaceutically acceptable carriers, diluents, or excipients, wherein the bispecific antibody comprises two first polypeptide chains and two second polypeptide chains wherein each of,
  a.) said first polypeptide chain comprises a single chain variable fragment (scFv) and a mAb IgG heavy chain (HC), the HC having a heavy chain variable region (HCVR1) comprising heavy chain CDRs (HCDR) 1-3 wherein the amino acid sequence of HCDR1 is SEQ ID NO:9, the amino acid sequence of HCDR2 is SEQ ID NO:10, the amino acid sequence of HCDR3 is SEQ ID NO:11, and the scFv having a heavy chain variable region (HCVR2) and a light chain variable region (LCVR2), HCVR2 comprising HCDRs 4-6 and LCVR2 comprising LCDRs 4-6, wherein the amino acid sequence of HCDR4 is SEQ ID NO:12, the amino acid sequence of HCDR5 is SEQ ID NO:13, the amino acid sequence of HCDR6 is SEQ ID NO:14, the amino acid sequence of LCDR4 is SEQ ID NO:18, the amino acid sequence of LCDR5 is SEQ ID NO:19, and the amino acid sequence of LCDR6 is SEQ ID NO:20; and
  b.) said second polypeptide comprises a mAb light chain (LC) having a LCVR1 comprising light chain CDRs (LCDR) 1-3, wherein the amino acid sequence of LCDR1 is SEQ ID NO:15, the amino acid sequence of LCDR2 is SEQ ID NO:16, the amino acid sequence of LCDR3 is SEQ ID NO:17,
  wherein each scFv is independently linked to said HC via polypeptide linker (L1) covalently attached to the N-terminus of HCVR2 and the C-terminus of HC, and LCVR2 is linked to HCVR2 of the same scFv via a second polypeptide linker (L2) covalently attached to the N-terminus of LCVR2 and the C-terminus of HCVR2.

6. The pharmaceutical composition of claim 5, wherein the amino acid sequence of HCVR1 of the bispecific antibody compound is SEQ ID NO:5, the amino acid sequence of LCVR1 of the bispecific antibody compound is SEQ ID NO:7, the amino acid sequence of HCVR2 of the bispecific antibody compound is SEQ ID NO:6, and the amino acid sequence of LCVR2 of the bispecific antibody compound is SEQ ID NO:8.

7. The pharmaceutical composition of claim 5, wherein the amino acid sequence of L1 of the bispecific antibody compound is SEQ ID NO: 21 and the amino acid sequence of L2 of the bispecific antibody compound is SEQ ID NO: 22.

8. The pharmaceutical composition of claim 5, wherein the amino acid sequence of each of the two first polypeptide chains is SEQ ID NO: 1 and the amino acid sequence of each of the two second polypeptide chains is SEQ ID NO: 2.

9. A method of treating at least one of osteoporosis, osteopenia, degenerative lumbar spondylolisthesis, degenerative disk disease, or osteogenesis imperfecta, comprising administering to a patient in need thereof a therapeutically effective amount of a bispecific antibody compound that binds DKK-1 and RANKL comprising two first polypeptide chains and two second polypeptide chains wherein each of,
  a.) said first polypeptide chain comprises a single chain variable fragment (scFv) and a mAb IgG heavy chain (HC), the HC having a heavy chain variable region (HCVR1) comprising heavy chain CDRs (HCDR) 1-3 wherein the amino acid sequence of HCDR1 is SEQ ID NO:9, the amino acid sequence of HCDR2 is SEQ ID NO:10, the amino acid sequence of HCDR3 is SEQ ID NO:11, and the scFv having a heavy chain variable region (HCVR2) and a light chain variable region (LCVR2), HCVR2 comprising HCDRs 4-6 and LCVR2 comprising LCDRs 4-6, wherein the amino acid sequence of HCDR4 is SEQ ID NO:12, the amino acid sequence of HCDR5 is SEQ ID NO:13, the amino acid sequence of HCDR6 is SEQ ID NO:14, the amino acid sequence of LCDR4 is SEQ ID NO:18, the amino acid sequence of LCDR5 is SEQ ID NO:19, and the amino acid sequence of LCDR6 is SEQ ID NO:20; and
  b.) said second polypeptide comprises a mAb light chain (LC) having a LCVR1 comprising light chain CDRs (LCDR) 1-3, wherein the amino acid sequence of LCDR1 is SEQ ID NO:15, the amino acid sequence of LCDR2 is SEQ ID NO:16, the amino acid sequence of LCDR3 is SEQ ID NO:17,
  wherein each scFv is independently linked to said HC via polypeptide linker (L1) covalently attached to the N-terminus of HCVR2 and the C-terminus of HC, and LCVR2 is linked to HCVR2 of the same scFv via a second polypeptide linker (L2) covalently attached to the N-terminus of LCVR2 and the C-terminus of HCVR2.

10. The method of claim 9, wherein the amino acid sequence of HCVR1 of the bispecific antibody compound is SEQ ID NO:5, the amino acid sequence of LCVR1 of the bispecific antibody compound is SEQ ID NO:7, the amino acid sequence of HCVR2 of the bispecific antibody compound is SEQ ID NO:6, and the amino acid sequence of LCVR2 of the bispecific antibody compound is SEQ ID NO:8.

11. The method of claim 9, wherein the amino acid sequence of L1 of the bispecific antibody compound is SEQ ID NO: 21 and the amino acid sequence of L2 of the bispecific antibody compound is SEQ ID NO: 22.

12. The method of claim 9, wherein the amino acid sequence of each of the two first polypeptide chains is SEQ ID NO: 1 and the amino acid sequence of each of the two second polypeptide chains is SEQ ID NO: 2.

* * * * *

SEQUENCE LISTING

```
<160> NUMBER OF SEQ ID NOS: 22

<210> SEQ ID NO 1
<211> LENGTH: 713
<212> TYPE: PRT
<213> ORGANISM: Artificial Sequence
<220> FEATURE:
<223> OTHER INFORMATION: synthetic construct of exemplified first
      polypeptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45
```

```
Ala Thr Ile Ser Gly Gly Phe Gly Thr Tyr Tyr Pro Asp Ser Val
    50              55                  60

Lys Gly Arg Phe Thr Ile Ser Arg Asp Asn Ala Lys Asn Ser Leu Tyr
 65              70              75                  80

Leu Gln Met Asn Ser Leu Arg Ala Glu Asp Thr Ala Val Tyr Tyr Cys
                 85              90                  95

Ala Arg Pro Gly Tyr Asn Asn Tyr Tyr Phe Asp Ile Trp Gly Gln Gly
            100             105             110

Thr Thr Val Thr Val Ser Ser Ala Ser Thr Lys Gly Pro Ser Val Phe
            115             120             125

Pro Leu Ala Pro Cys Ser Arg Ser Thr Ser Glu Ser Thr Ala Ala Leu
130             135             140

Gly Cys Leu Val Lys Asp Tyr Phe Pro Glu Pro Val Thr Val Ser Trp
145             150             155             160

Asn Ser Gly Ala Leu Thr Ser Gly Val His Thr Phe Pro Ala Val Leu
                165             170             175

Gln Ser Ser Gly Leu Tyr Ser Leu Ser Ser Val Val Thr Val Pro Ser
            180             185             190

Ser Ser Leu Gly Thr Lys Thr Tyr Thr Cys Asn Val Asp His Lys Pro
    195             200             205

Ser Asn Thr Lys Val Asp Lys Arg Val Glu Ser Lys Tyr Gly Pro Pro
210             215             220

Cys Pro Pro Cys Pro Ala Pro Glu Ala Ala Gly Gly Pro Ser Val Phe
225             230             235             240

Leu Phe Pro Pro Lys Pro Lys Asp Thr Leu Met Ile Ser Arg Thr Pro
                245             250             255

Glu Val Thr Cys Val Val Val Asp Val Ser Gln Glu Asp Pro Glu Val
            260             265             270

Gln Phe Asn Trp Tyr Val Asp Gly Val Glu Val His Asn Ala Lys Thr
            275             280             285

Lys Pro Arg Glu Glu Gln Phe Asn Ser Thr Tyr Arg Val Val Ser Val
290             295             300

Leu Thr Val Leu His Gln Asp Trp Leu Asn Gly Lys Glu Tyr Lys Cys
305             310             315             320

Lys Val Ser Asn Lys Gly Leu Pro Ser Ser Ile Glu Lys Thr Ile Ser
                325             330             335

Lys Ala Lys Gly Gln Pro Arg Glu Pro Gln Val Tyr Thr Leu Pro Pro
            340             345             350

Ser Gln Glu Glu Met Thr Lys Asn Gln Val Ser Leu Thr Cys Leu Val
    355             360             365

Lys Gly Phe Tyr Pro Ser Asp Ile Ala Val Glu Trp Glu Ser Asn Gly
370             375             380

Gln Pro Glu Asn Asn Tyr Lys Thr Thr Pro Pro Val Leu Asp Ser Asp
385             390             395             400

Gly Ser Phe Phe Leu Tyr Ser Arg Leu Thr Val Asp Lys Ser Arg Trp
                405             410             415

Gln Glu Gly Asn Val Phe Ser Cys Ser Val Met His Glu Ala Leu His
            420             425             430

Asn His Tyr Thr Gln Lys Ser Leu Ser Leu Ser Leu Gly Gly Gly Gly
            435             440             445

Gly Ser Gly Gly Gly Gly Ser Gly Gly Gly Gly Ser Gln Val Gln Leu
    450             455             460
```

```
Val Gln Ser Gly Ala Glu Val Lys Lys Pro Gly Ser Ser Val Lys Val
465                 470                 475                 480

Ser Cys Lys Ala Ser Gly Tyr Ala Phe Thr Asn Tyr Tyr Ile Glu Trp
            485                 490                 495

Val Arg Gln Ala Pro Gly Gln Cys Leu Glu Trp Met Gly Val Ile Asn
        500                 505                 510

Pro Gly Trp Gly Asp Thr Asn Tyr Asn Glu Lys Phe Lys Gly Arg Val
    515                 520                 525

Thr Ile Thr Ala Asp Lys Ser Thr Ser Thr Ala Tyr Met Glu Leu Ser
530                 535                 540

Ser Leu Arg Ser Glu Asp Thr Ala Val Tyr Tyr Cys Ala Arg Arg Asp
545                 550                 555                 560

Thr Ala His Gly Tyr Tyr Ala Leu Asp Pro Trp Gly Gln Gly Thr Thr
                565                 570                 575

Val Thr Val Ser Ser Gly Gly Gly Ser Gly Gly Gly Gly Ser Gly
                580                 585                 590

Gly Gly Gly Ser Gly Gly Gly Gly Ser Gly Gly Gly Gly Ser Asp Ile
            595                 600                 605

Gln Met Thr Gln Ser Pro Ser Ser Leu Ser Ala Ser Val Gly Asp Arg
    610                 615                 620

Val Thr Ile Thr Cys Lys Ala Ser Gln Asn Val Gly Thr Asn Val Ala
625                 630                 635                 640

Trp Tyr Gln Gln Lys Pro Gly Lys Ala Pro Lys Leu Leu Ile Tyr Ser
                645                 650                 655

Ala Ser Tyr Arg Tyr Ser Gly Val Pro Ser Arg Phe Ser Gly Ser Gly
                660                 665                 670

Ser Gly Thr Asp Phe Thr Leu Thr Ile Ser Ser Leu Gln Pro Glu Asp
            675                 680                 685

Phe Ala Thr Tyr Tyr Cys Gln Gln Tyr Trp Asp Tyr Pro Leu Thr Phe
        690                 695                 700

Gly Cys Gly Thr Lys Val Glu Ile Lys
705                 710

<210> SEQ ID NO 2
<211> LENGTH: 214
<212> TYPE: PRT
<213> ORGANISM: Artificial Sequence
<220> FEATURE:
<223> OTHER INFORMATION: synthetic construct of exemplified second
      polypeptide

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys His Ala Ser Asp Ser Ile Ser Asn Ser
                20                  25                  30

Leu His Trp Tyr Gln Gln Lys Pro Gly Gln Ala Pro Arg Leu Leu Ile
            35                  40                  45

Tyr Tyr Ala Arg Gln Ser Ile Gln Gly Ile Pro Ala Arg Phe Ser Gly
        50                  55                  60

Ser Gly Ser Gly Thr Asp Phe Leu Thr Ile Ser Ser Leu Glu Pro
65                  70                  75                  80

Glu Asp Phe Ala Val Tyr Tyr Cys Gln Gln Ser Glu Ser Trp Pro Leu
                85                  90                  95

His Phe Gly Gly Gly Thr Lys Val Glu Ile Lys Arg Thr Val Ala Ala
                100                 105                 110
```

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 3
<211> LENGTH: 2199
<212> TYPE: DNA
<213> ORGANISM: Artificial Sequence
<220> FEATURE:
<223> OTHER INFORMATION: synthetic construct of DNA encoding the
      exemplified first polypeptide with a signal peptide

<400> SEQUENCE: 3

| | | | | |
|---|---|---|---|---|
| atggagacgg | acactctcct | cctgtgggta | ttgctccttt | gggtccctgg ttctacaggg | 60 |
| gaggtacagc | tggtagaaag | cggtggggga | ttggtacaac | aggtggatc tctccggttg | 120 |
| tcatgtgcag | ctagtgggtt | taccttctcc | agttatacga | tgtcttgggt gagacaagcg | 180 |
| cccggtaaag | gattggagtg | ggtcgcaacc | atcagtggag | agggtttgg aacatactac | 240 |
| cctgatagcg | ttaaggggcg | gtttaccata | agcagagata | acgcgaagaa ctctctctac | 300 |
| cttcaaatga | actctctgcg | ggctgaagat | acagctgtgt | attattgcgc ccgccctggg | 360 |
| tataacaatt | actacttcga | tatttggggc | caagggacaa | ccgtaaccgt gtctagcgct | 420 |
| tcaactaagg | gtccaagcgt | gttccctttg | gcaccctgca | gcagaagcac gtccgagtct | 480 |
| accgctgctt | gggctgtgct | cgtcaaggac | tacttccccg | aaccagttac tgtttcttgg | 540 |
| aactctggtg | cactcacaag | tggggtccat | acgttccccg | ccgttttgca atccagcggg | 600 |
| ttgtactctc | tttcatccgt | ggtcactgtt | cctagctcca | gcctcggcac taaaacttac | 660 |
| acttgtaatg | tagaccataa | gcccagcaac | accaaggtgg | ataagagagt cgagtccaag | 720 |
| tacggccctc | cttgtcctcc | atgtcctgcg | ccggaggccg | ccggaggacc ttctgtgttc | 780 |
| cttttttccac | caaaacctaa | agacacctt | atgatatccc | gaactcccga ggtaacgtgc | 840 |
| gtggtagtcg | atgtaagcca | ggaagatccc | gaagtccagt | tcaattggta cgttgacggc | 900 |
| gtcgaagtcc | acaatgctaa | gacaaaaccc | agggaagagc | agttcaacag cacctatcgc | 960 |
| gtagtgagcg | tactgaccgt | gcttcaccaa | gactggctca | acggtaagga atataaatgt | 1020 |
| aaggtttcca | ataaaggcct | gcccagctca | attgagaaaa | ccatatccaa agctaagggg | 1080 |
| caacctcgag | aaccacaggt | ttacacactt | cctccatcac | aggaggaaat gacgaaaaat | 1140 |
| caggttagcc | tgacttgtct | cgttaaagga | ttttatccat | ctgatattgc cgtagaatgg | 1200 |
| gagagtaatg | gacagcctga | gaataactat | aagaccacac | cacccgtcct cgactctgac | 1260 |
| ggctcattct | tcctgtattc | tcgcttgacg | gtggacaaga | gcagatggca ggaagggaac | 1320 |
| gtgttttctt | gcagtgtgat | gcacgaggca | ctgcataatc | attacacaca gaagtctttg | 1380 |
| tccctgtcac | tgggtggcgg | aggaggttca | ggaggtgggg | gcagtggcgg cggaggctca | 1440 |

-continued

```
caggtccagc ttgtccagtc tggggcagag gtgaagaagc ccgggagtag tgtgaaggtc   1500
agctgtaagg cgtcagggta cgcttttact aattactaca ttgaatgggt gagacaggct   1560
ccaggccagt gtcttgagtg gatgggcgtg attaatccag gctggggtga cactaattac   1620
aatgagaagt tcaaagggcg ggtgactatc acggcagata agtctacttc cactgcttat   1680
atggagctct cctccctgag gagcgaagac accgctgttt attattgtgc ccggcgagat   1740
acagcccatg ggtattatgc cctcgatcca tggggccagg gcacgacagt taccgtgagc   1800
tccggaggag gagggagcgg gggcggggga tctggaggag gaggaagtgg aggtggaggg   1860
tctgggggag gcggaagcga tatccagatg actcaaagcc ctagttcctt gagcgcctct   1920
gtgggcgaca gagtgacaat aacctgtaaa gcatcacaaa acgtgggcac caacgtggcg   1980
tggtatcaac aaaaacctgg caaggcgcct aagttgctga tttatagtgc atcttacagg   2040
tattcagggg tgccctccag atttagtggc agtggcagcg gaaccgattt cactctcaca   2100
ataagctctc ttcagccaga ggacttcgcg acgtattatt gccaacagta ttgggactat   2160
ccactgactt tcggttgtgg aacaaaggtt gagatcaag                          2199
```

```
<210> SEQ ID NO 4
<211> LENGTH: 702
<212> TYPE: DNA
<213> ORGANISM: Artificial Sequence
<220> FEATURE:
<223> OTHER INFORMATION: synthetic construct of DNA encoding exemplified
      second polypeptide with a signal peptide

<400> SEQUENCE: 4
atggagacag acacactcct gctatgggta ctgctgctct gggttccagg atccactggt     60
gaaattgtgt tgacacagtc tccagccacc ctgtctttgt ctccagggga aagagccacc    120
ctctcctgcc acgccagcga cagtattagc aacagcctac actggtacca acagaaacct    180
ggccaggctc ccaggctcct catctattat gctagacagt ccatccaggg catcccagcc    240
aggttcagtg gcagtgggtc tgggacagac ttcactctca ccatcagcag cctagagcct    300
gaagattttg cagtttatta ctgtcaacag agtgagagct ggccgctcca cttcggcgga    360
gggaccaagg tggagatcaa acgaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagctcgc ccgtcacaaa gagcttcaac aggggagagt gc                       702
```

```
<210> SEQ ID NO 5
<211> LENGTH: 119
<212> TYPE: PRT
<213> ORGANISM: Artificial Sequence
<220> FEATURE:
<223> OTHER INFORMATION: synthetic construct of exemplified HCVR1

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45
```

```
Ala Thr Ile Ser Gly Gly Gly Phe Gly Thr Tyr Tyr Pro Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Pro Gly Tyr Asn Asn Tyr Tyr Phe Asp Ile Trp Gly Gln Gly
            100                 105                 110

Thr Thr Val Thr Val Ser Ser
            115

<210> SEQ ID NO 6
<211> LENGTH: 121
<212> TYPE: PRT
<213> ORGANISM: Artificial Sequence
<220> FEATURE:
<223> OTHER INFORMATION: synthetic construct of exemplified HCVR2

<400> SEQUENCE: 6

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ala Phe Thr Asn Tyr
                 20                  25                  30

Tyr Ile Glu Trp Val Arg Gln Ala Pro Gly Gln Cys Leu Glu Trp Met
             35                  40                  45

Gly Val Ile Asn Pro Gly Trp Gly Asp Thr Asn Tyr Asn Glu Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Asp Thr Ala His Gly Tyr Tyr Ala Leu Asp Pro Trp Gly
            100                 105                 110

Gln Gly Thr Thr Val Thr Val Ser Ser
            115                 120

<210> SEQ ID NO 7
<211> LENGTH: 107
<212> TYPE: PRT
<213> ORGANISM: Artificial Sequence
<220> FEATURE:
<223> OTHER INFORMATION: synthetic construct of exemplified LCVR1

<400> SEQUENCE: 7

Glu Ile Val Leu Thr Gln Ser Pro Ala Thr Leu Ser Leu Ser Pro Gly
 1               5                  10                  15

Glu Arg Ala Thr Leu Ser Cys His Ala Ser Asp Ser Ile Ser Asn Ser
                 20                  25                  30

Leu His Trp Tyr Gln Gln Lys Pro Gly Gln Ala Pro Arg Leu Leu Ile
             35                  40                  45

Tyr Tyr Ala Arg Gln Ser Ile Gln Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Glu Ser Trp Pro Leu
                 85                  90                  95

His Phe Gly Gly Gly Thr Lys Val Glu Ile Lys
            100                 105
```

```
<210> SEQ ID NO 8
<211> LENGTH: 107
<212> TYPE: PRT
<213> ORGANISM: Artificial Sequence
<220> FEATURE:
<223> OTHER INFORMATION: synthetic construct of exemplified LCVR2

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Asp Tyr Pro Leu
                85                  90                  95

Thr Phe Gly Cys Gly Thr Lys Val Glu Ile Lys
            100                 105

<210> SEQ ID NO 9
<211> LENGTH: 13
<212> TYPE: PRT
<213> ORGANISM: Artificial Sequence
<220> FEATURE:
<223> OTHER INFORMATION: synthetic construct of exemplified HCDR1

<400> SEQUENCE: 9

Ala Ala Ser Gly Phe Thr Phe Ser Ser Tyr Thr Met Ser
1               5                   10

<210> SEQ ID NO 10
<211> LENGTH: 17
<212> TYPE: PRT
<213> ORGANISM: Artificial Sequence
<220> FEATURE:
<223> OTHER INFORMATION: synthetic construct of exemplified HCDR2

<400> SEQUENCE: 10

Thr Ile Ser Gly Gly Gly Phe Gly Thr Tyr Tyr Pro Asp Ser Val Lys
1               5                   10                  15

Gly

<210> SEQ ID NO 11
<211> LENGTH: 12
<212> TYPE: PRT
<213> ORGANISM: Artificial Sequence
<220> FEATURE:
<223> OTHER INFORMATION: synthetic construct of exemplified HCDR3

<400> SEQUENCE: 11

Ala Arg Pro Gly Tyr Asn Asn Tyr Tyr Phe Asp Ile
1               5                   10

<210> SEQ ID NO 12
<211> LENGTH: 13
<212> TYPE: PRT
<213> ORGANISM: Artificial Sequence
<220> FEATURE:
<223> OTHER INFORMATION: synthetic construct of exemplified HCDR4
```

```
<400> SEQUENCE: 12

Lys Ala Ser Gly Tyr Ala Phe Thr Asn Tyr Tyr Ile Glu
1               5                   10

<210> SEQ ID NO 13
<211> LENGTH: 17
<212> TYPE: PRT
<213> ORGANISM: Artificial Sequence
<220> FEATURE:
<223> OTHER INFORMATION: synthetic construct of exemplified HCDR5

<400> SEQUENCE: 13

Val Ile Asn Pro Gly Trp Gly Asp Thr Asn Tyr Asn Glu Lys Phe Lys
1               5                   10                  15

Gly

<210> SEQ ID NO 14
<211> LENGTH: 14
<212> TYPE: PRT
<213> ORGANISM: Artificial Sequence
<220> FEATURE:
<223> OTHER INFORMATION: synthetic construct of exemplified HCDR6

<400> SEQUENCE: 14

Ala Arg Arg Asp Thr Ala His Gly Tyr Tyr Ala Leu Asp Pro
1               5                   10

<210> SEQ ID NO 15
<211> LENGTH: 11
<212> TYPE: PRT
<213> ORGANISM: Artificial Sequence
<220> FEATURE:
<223> OTHER INFORMATION: synthetic construct of exemplified LCDR1

<400> SEQUENCE: 15

His Ala Ser Asp Ser Ile Ser Asn Ser Leu His
1               5                   10

<210> SEQ ID NO 16
<211> LENGTH: 8
<212> TYPE: PRT
<213> ORGANISM: Artificial Sequence
<220> FEATURE:
<223> OTHER INFORMATION: synthetic construct exemplified LCDR2

<400> SEQUENCE: 16

Tyr Tyr Ala Arg Gln Ser Ile Gln
1               5

<210> SEQ ID NO 17
<211> LENGTH: 9
<212> TYPE: PRT
<213> ORGANISM: Artificial Sequence
<220> FEATURE:
<223> OTHER INFORMATION: synthetic construct of exemplified LCDR3

<400> SEQUENCE: 17

Gln Gln Ser Glu Ser Trp Pro Leu His
1               5

<210> SEQ ID NO 18
<211> LENGTH: 11
<212> TYPE: PRT
<213> ORGANISM: Artificial Sequence
<220> FEATURE:
<223> OTHER INFORMATION: synthetic construct of exemplified LCDR4
```

```
<400> SEQUENCE: 18

Lys Ala Ser Gln Asn Val Gly Thr Asn Val Ala
1               5                   10

<210> SEQ ID NO 19
<211> LENGTH: 8
<212> TYPE: PRT
<213> ORGANISM: Artificial Sequence
<220> FEATURE:
<223> OTHER INFORMATION: synthetic construct of exemplified LCDR5

<400> SEQUENCE: 19

Tyr Ser Ala Ser Tyr Arg Tyr Ser
1               5

<210> SEQ ID NO 20
<211> LENGTH: 9
<212> TYPE: PRT
<213> ORGANISM: Artificial Sequence
<220> FEATURE:
<223> OTHER INFORMATION: synthetic construct of LCDR6

<400> SEQUENCE: 20

Gln Gln Tyr Trp Asp Tyr Pro Leu Thr
1               5

<210> SEQ ID NO 21
<211> LENGTH: 15
<212> TYPE: PRT
<213> ORGANISM: Artificial Sequence
<220> FEATURE:
<223> OTHER INFORMATION: synthetic construct of exemplified L1

<400> SEQUENCE: 21

Gly Gly Gly Gly Ser Gly Gly Gly Gly Ser Gly Gly Gly Gly Ser
1               5                   10                  15

<210> SEQ ID NO 22
<211> LENGTH: 25
<212> TYPE: PRT
<213> ORGANISM: Artificial Sequence
<220> FEATURE:
<223> OTHER INFORMATION: synthetic construct of exemplified L2

<400> SEQUENCE: 22

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```